United States Patent
Thomas et al.

(10) Patent No.: US 11,679,159 B2
(45) Date of Patent: Jun. 20, 2023

(54) COMPOSITIONS FOR TRANSFECTING RESISTANT CELL TYPES

(71) Applicant: Precision Nanosystems ULC, Vancouver (CA)

(72) Inventors: Anitha Thomas, New Westminster (CA); Andrew William Brown, Vancouver (CA); Rebecca Anne Grace De Souza, Vancouver (CA); Tara L. Fernandez, Vancouver (CA)

(73) Assignee: Precision Nanosystems ULC, Vancouver (CA)

( * ) Notice: Subject to any disclaimer, the term of this patent is extended or adjusted under 35 U.S.C. 154(b) by 94 days.

(21) Appl. No.: 17/051,572

(22) PCT Filed: Apr. 15, 2019

(86) PCT No.: PCT/CA2019/050456
§ 371 (c)(1),
(2) Date: Oct. 29, 2020

(87) PCT Pub. No.: WO2019/210394
PCT Pub. Date: Nov. 7, 2019

(65) Prior Publication Data
US 2021/0162052 A1   Jun. 3, 2021

Related U.S. Application Data

(60) Provisional application No. 62/664,208, filed on Apr. 29, 2018.

(51) Int. Cl.
| | | |
|---|---|---|
| A61K 47/28 | (2006.01) | |
| A61K 47/26 | (2006.01) | |
| A61K 48/00 | (2006.01) | |

(52) U.S. Cl.
CPC .............. *A61K 47/28* (2013.01); *A61K 47/26* (2013.01); *A61K 48/0008* (2013.01)

(58) Field of Classification Search
None
See application file for complete search history.

(56) References Cited

U.S. PATENT DOCUMENTS

| | | |
|---|---|---|
| 5,753,613 A | 5/1998 | Ansell et al. |
| 6,734,171 B1 | 5/2004 | Saravolac et al. |
| 7,479,573 B2 | 1/2009 | Chu et al. |
| D771,833 S | 11/2016 | Leaver et al. |
| D771,834 S | 11/2016 | Leaver et al. |
| D772,427 S | 11/2016 | Leaver et al. |
| 9,758,795 B2 | 9/2017 | Cullis et al. |
| D800,335 S | 10/2017 | Chang et al. |
| D800,336 S | 10/2017 | Chang et al. |
| D803,416 S | 11/2017 | Leaver et al. |
| D812,242 S | 3/2018 | Chang et al. |
| 9,943,846 B2 | 4/2018 | Cullis et al. |
| 10,076,730 B2 | 9/2018 | Wild et al. |
| 2002/0169138 A1* | 11/2002 | Kunz ................... A61K 9/1075 514/44 R |
| 2004/0026223 A1 | 2/2004 | Schmidt et al. |
| 2010/0309986 A1 | 12/2010 | Fujisawa |
| 2016/0022580 A1 | 1/2016 | Ramsay et al. |
| 2016/0235688 A1 | 8/2016 | Walsh et al. |
| 2016/0317647 A1* | 11/2016 | Ciaramella ........ A61K 31/7105 |
| 2018/0000953 A1 | 1/2018 | Almarsson et al. |
| 2018/0093232 A1 | 4/2018 | Wild et al. |
| 2018/0221510 A1 | 8/2018 | Manoharan et al. |

FOREIGN PATENT DOCUMENTS

| | | |
|---|---|---|
| WO | 2009/028824 A2 | 3/2009 |
| WO | 2009/096558 A1 | 8/2009 |
| WO | 2012016184 A2 | 2/2012 |
| WO | 2014/172045 A1 | 10/2014 |
| WO | 2015/057998 A1 | 4/2015 |
| WO | 2017/117647 A1 | 7/2017 |
| WO | 2017/117764 A1 | 7/2017 |
| WO | 2017/218704 A1 | 12/2017 |
| WO | 2018/006166 A1 | 1/2018 |
| WO | 2018/064755 A1 | 4/2018 |
| WO | 2018/089540 A1 | 5/2018 |
| WO | 2019/046809 A1 | 3/2019 |

OTHER PUBLICATIONS

Akhtar, S. et al. Interactions of antisense DNA olgionucleotide analogs with phodpholipid membranes (liposomes), Nucleic Acid Research, 1991, pp. 5551-5559, vol. 19, No. 20.

Bunjes, H. et al. "Effects of surfactants on the crystallization and polymorphism of lipid nanoparticles" Progr Colloid Polym Sci, 2002 pp. 7-10, vol. 121.

Garg, S. et al. "Microfluidics: a transformational tool for nanomedicine development and production", Journal of Drug Targeting, 2016, pp. 821-835, vol. 24, No. 9.

Ge, X. et al. "Advances of non-Ionic Surfactant Vesicles (Niosomes) and Their Application in Drug Delivery", Pharmaceutics, 2019, pp. 1-16, vol. 11, No. 55.

Kauffman, KJ et al. "DG. Materials for non-viral intracellular delivery of messenger RNA therapeutics" J Control Release. Oct. 28, 2016;240:227-234. doi: 10.1016/j.jconrel.2015.12.032. Epub Dec. 21, 2015. PMID: 26718856.

Kauffman, K. J. et al. "Optimization of Lipid Nanoparticle Formulations for mRNA Delivery in Vivo with Fractional Factorial and Definitive Screening Designs" Nano letters, 2015, 15(11), 7300-7306.

(Continued)

*Primary Examiner* — Robert A Wax
*Assistant Examiner* — Quanglong N Truong
(74) *Attorney, Agent, or Firm* — Leydig, Voit & Mayer, Ltd.

(57) ABSTRACT

A reagent composition for delivery nucleic acid therapeutics to cells is provided. The reagent includes ionizable lipid, structural lipid, and a stabilizing agent which improves the transfection efficiency of nucleic acids, and leaves transfected cells viable. The 5 transfection reagent is effective in plasmid and mRNA delivery, and in neurons and progenitor-like cells. It may be used for ex vivo cell therapy.

19 Claims, 9 Drawing Sheets
Specification includes a Sequence Listing.

(56) References Cited

OTHER PUBLICATIONS

Lv, H. et al. "Toxicity of cationic lipids and cationic polymers in gene delivery. Journal of controlled release : official journal of the Controlled Release Society" 2016, 114(1), 100-109.

Mingozzi, F. et al. "Immune Responses to AAV vectods: overcoming barriers to successful gene therapy" Blood, 2013, pp. 23-36, vol. 122, No. 1.

O'Mahony, A. M., et al. "Non-viral nanosystems for gene and small interfering RNA delivery to the central nervous system: formulating the solution", Journal of pharmaceutical sciences, 2013, 102(10), 3469-3484.

Tam, Y. et al. "Advances in Lipid Nanoparticles for siRNA Delivery" Pharmaceutics, 2013, pp. 498-507, vol. 5.

* cited by examiner

SEQUENCE LISTING

<160> NUMBER OF SEQ ID NOS: 2

<210> SEQ ID NO 1
<211> LENGTH: 5514
<212> TYPE: DNA
<213> ORGANISM: Artificial
<220> FEATURE:
<223> OTHER INFORMATION: Circular dsDNA pCX-EGFP

<400> SEQUENCE: 1

```
gtcgacattg attattgact agttattaat agtaatcaat tacggggtca ttagttcata         60
gcccatatat ggagttccgc gttacataac ttacggtaaa tggcccgcct ggctgaccgc        120
ccaacgaccc ccgcccattg acgtcaataa tgacgtatgt tcccatagta acgccaatag        180
ggactttcca ttgacgtcaa tgggtggact atttacggta aactgcccac ttggcagtac        240
atcaagtgta tcatatgcca agtacgcccc ctattgacgt caatgacggt aaatggcccg        300
cctggcatta tgcccagtac atgaccttat gggactttcc tacttggcag tacatctacg        360
tattagtcat cgctattacc atgggtcgag gtgagcccca cgttctgctt cactctcccc        420
atctcccccc cctccccacc cccaattttg tatttattta ttttttaatt attttgtgca        480
gcgatggggg cggggggggg ggggcgcgc gccaggcggg gcgggcggg gcgaggggcg        540 gggcggggcg aggcggagag gtgcggcggc agccaatcag agcggcgcgc tccgaaagtt        600
tccttttatg gcgaggcggc ggcggcggcg gcccataaaa agcgaagcg cgcggcgggc        660 gggagtcgct gcgttgcctt cgccccgtgc cccgctccgc gccgcctcgc gccgcccgcc        720
ccggctctga ctgaccgcgt tactcccaca ggtgagcggg cgggacggcc cttctcctcc        780
gggctgtaat tagcgcttgg tttaatgacg gctcgttttct tttctgtggc tgcgtgaaag        840
ccttaaaggg ctccgggagg gcccttttgtg cggggggggag cggctcgggg ggtgcgtgcg        900
tgtgtgtgtg cgtgggggagc gccgcgtgcg gcccgcgctg cccggcggct gtgagcgctg        960
cgggcgcggc gcgggcttt gtgcgctccg cgtgtgcgcg aggggagcgc ggccgggggc       1020
ggtgccccgc ggtgcggggg ggctgcgagg ggaacaaagg ctgcgtgcgg ggtgtgtgcg       1080
tgggggggtg agcaggggt gtgggcgcgg cggtcgggct gtaacccccc cctgcacccc       1140
cctccccgag ttgctgagca cggcccggct tcgggtgcgg ggctccgtac ggggcgtggc       1200
gcggggctcg ccgtgccggg cgggggtgg cggcaggtgg gggtgccggg cggggcgggg       1260
ccgcctcggg ccggggaggg ctcggggag gggcgcggcg gcccccggag cgccggcggc       1320
tgtcgaggcg cggcgagccg cagccattgc ctttttatggt aatcgtgcga gagggcgcag       1380
ggacttcctt tgtcccaaat ctgtgcggag ccgaaatctg ggaggcgccg ccgcaccccc       1440
tctagcgggc gcggggcgaa gcggtgcggc gccggcagga aggaactggg cggggagggc       1500
cttcgtgcgt cgccgcgccg ccgtcccctt ctccctctcc agcctcgggg ctgtccgcgg       1560
ggggacggct gccttcgggg gggacgggc agggcgggt tcggcttctg gcgtgtgacc       1620
ggcggctcta gagcctctgc taaccatgtt catgccttct tcttttttcct acagctcctg       1680 ggcaacgtgc tggttattgt gctgtctcat cattttggca aagaattcgc caccatggtg       1740
agcaagggcg aggagctgtt caccggggtg gtgcccatcc tggtcgagct ggacggcgac       1800
gtgaacggcc acaagttcag cgtgtccggc gagggcgagg gcgatgccac ctacggcaag       1860
ctgaccctga agttcatctg caccaccggc aagctgcccg tgccctggcc cacccccgtg       1920
accaccctga cctacggcgt gcagtgcttc agccgctacc ccgaccacat gaagcagcac       1980
gacttcttca gtccgccat gcccgaaggc tacgtccagg agcgcaccat cttcttcaag       2040
gacgacggca actacaagac ccgcgccgag gtgaagttcg agggcgacac cctggtgaac       2100
cgcatcgagc tgaagggcat cgacttcaag gaggacggca acatcctggg gcacaagctg       2160
gagtacaact acaacagcca caacgtctat atcatggccg acaagcagaa gaacggcatc       2220
aaggtgaact tcaagatccg ccacaacatc gaggacggca gcgtgcagct cgccgaccac       2280
taccagcaga acacccccat cggcgacggc ccgtgctgc tgcccgacaa ccactacctg       2340
agcacccagt ccgccctgag caaagacccc aacgagaagc gcgatcacat ggtcctgctg       2400
```

```
gagttcgtga ccgccgccgg gatcactcac ggcatggacg agctgtacaa gtaagaattc    2460
actcctcagg tgcaggctgc ctatcagaag gtggtggctg gtgtggccaa tgccctggct    2520
cacaaatacc actgagatct ttttccctct gccaaaaatt atggggacat catgaagccc    2580
cttgagcatc tgacttctgg ctaataaagg aaatttattt tcattgcaat agtgtgttgg    2640 aatttttttgt gtctctcact cggaaggaca tatgggaggg caaatcattt aaaacatcag    2700
aatgagtatt tggtttagag tttggcaaca tatgccatat gctggctgcc atgaacaaag    2760
gtggctataa agaggtcatc agtatatgaa acagcccct gctgtccatt ccttattcca    2820
tagaaaagcc ttgacttgag gttagatttt ttttatattt tgttttgtgt tattttttc    2880 tttaacatcc ctaaaatttt ccttacatgt tttactagcc agattttttcc tcctctcctg    2940 actactccca gtcatagctg tccctcttct cttatgaaga tccctcgacc tgcagcccaa    3000
gcttggcgta atcatggtca tagctgtttc ctgtgtgaaa ttgttatccg ctcacaattc    3060
cacacaacat acgagccgga agcataaagt gtaaagcctg gggtgcctaa tgagtgagct    3120
aactcacatt aattgcgttg cgctcactgc ccgctttcca gtcgggaaac ctgtcgtgcc    3180
agcggatccg catctcaatt agtcagcaac catagtcccg cccctaactc cgcccatccc    3240
gcccctaact ccgcccagtt ccgcccattc tccgccccat ggctgactaa ttttttttat    3300
ttatgcagag gccgaggccg cctcggcctc tgagctattc cagaagtagt gaggaggctt    3360
ttttggaggc ctaggctttt gcaaaaagct aacttgttta ttgcagctta taatggttac    3420
aaataaagca atagcatcac aaatttcaca aataaagcat ttttttcact gcattctagt    3480
tgtggtttgt ccaaactcat caatgtatct tatcatgtct ggatccgctg cattaatgaa    3540
tcggccaacg cgcggggaga ggcggtttgc gtattgggcg ctcttccgct tcctcgctca    3600
ctgactcgct gcgctcggtc gttcggctgc ggcgagcggt atcagctcac tcaaaggcgg    3660
taatacggtt atccacagaa tcaggggata acgcaggaaa gaacatgtga gcaaaaggcc    3720
agcaaaaggc caggaaccgt aaaaaggccg cgttgctggc gtttttccat aggctccgcc    3780
cccctgacga gcatcacaaa aatcgacgct caagtcagag gtggcgaaac ccgacaggac    3840
tataaagata ccaggcgttt ccccctggaa gctccctcgt gcgctctcct gttccgaccc    3900
tgccgcttac cggatacctg tccgcctttc tcccttcggg aagcgtggcg ctttctcaat    3960
gctcacgctg taggtatctc agttcggtgt aggtcgttcg ctccaagctg ggctgtgtgc    4020
acgaaccccc cgttcagccc gaccgctgcg ccttatccgg taactatcgt cttgagtcca    4080
acccggtaag acacgactta tcgccactgg cagcagccac tggtaacagg attagcagag    4140
cgaggtatgt aggcggtgct acagagttct tgaagtggtg gcctaactac ggctacacta    4200
gaaggacagt atttggtatc tgcgctctgc tgaagccagt taccttcgga aaagagttg    4260 gtagctcttg atccggcaaa caaaccaccg ctggtagcgg tggttttttt gtttgcaagc    4320
agcagattac gcgcagaaaa aaaggatctc aagaagatcc tttgatcttt tctacggggt    4380
ctgacgctca gtggaacgaa aactcacgtt aagggatttt ggtcatgaga ttatcaaaaa    4440
ggatcttcac ctagatcctt ttaaattaaa aatgaagttt taaatcaatc taaagtatat    4500
atgagtaaac ttggtctgac agttaccaat gcttaatcag tgaggcacct atctcagcga    4560
tctgtctatt tcgttcatcc atagttgcct gactccccgt cgtgtagata actacgatac    4620
gggagggctt accatctggc cccagtgctg caatgatacc gcgagaccca cgctcaccgg    4680
ctccagattt atcagcaata aaccagccag ccggaagggc cgagcgcaga agtggtcctg    4740
```

| | |
|---|---|
| caactttatc cgcctccatc cagtctatta attgttgccg ggaagctaga gtaagtagtt | 4800 |
| cgccagttaa tagtttgcgc aacgttgttg ccattgctac aggcatcgtg gtgtcacgct | 4860 |
| cgtcgtttgg tatggcttca ttcagctccg gttcccaacg atcaaggcga gttacatgat | 4920 |
| cccccatgtt gtgcaaaaaa gcggttagct ccttcggtcc tccgatcgtt gtcagaagta | 4980 |
| agttggccgc agtgttatca ctcatggtta tggcagcact gcataattct cttactgtca | 5040 |
| tgccatccgt aagatgcttt tctgtgactg gtgagtactc aaccaagtca ttctgagaat | 5100 |
| agtgtatgcg gcgaccgagt tgctcttgcc cggcgtcaat acgggataat accgcgccac | 5160 |
| atagcagaac tttaaaagtg ctcatcattg gaaaacgttc ttcggggcga aaactctcaa | 5220 |
| ggatcttacc gctgttgaga tccagttcga tgtaacccac tcgtgcaccc aactgatctt | 5280 |
| cagcatcttt tactttcacc agcgtttctg ggtgagcaaa aacaggaagg caaaatgccg | 5340 |
| caaaaaaggg aataagggcg acacggaaat gttgaatact catactcttc cttttttcaat | 5400 |
| attattgaag catttatcag ggttattgtc tcatgagcgg atacatattt gaatgtattt | 5460 |
| agaaaaataa acaaataggg gttccgcgca catttccccg aaaagtgcca cctg | 5514 |

<210> SEQ ID NO 2
<211> LENGTH: 966
<212> TYPE: DNA
<213> ORGANISM: Artificial
<220> FEATURE:
<223> OTHER INFORMATION: mRNA eGFP ORF
<220> FEATURE:
<221> NAME/KEY: misc_feature
<222> LOCATION: (721)..(846)
<223> OTHER INFORMATION: n is a, c, g, t or u

<400> SEQUENCE: 2

| | |
|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccctgaccta cggcgtgcag tgcttcagcc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaagtaa | 720 |
| nnnnnnnnnn nnnnnnnnnn nnnnnnnnnn nnnnnnnnnn nnnnnnnnnn nnnnnnnnnn | 780 |
| nnnnnnnnnn nnnnnnnnnn nnnnnnnnnn nnnnnnnnnn nnnnnnnnnn nnnnnnnnnn | 840 |
| nnnnnnaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaaaaaa | 960 |
| aaaaaa | 966 |

COMPOSITIONS FOR TRANSFECTING RESISTANT CELL TYPES

BACKGROUND OF THE INVENTION

Field of Invention

The field of the invention is the transfer of active nucleic acids into cells.

Related art

Nucleic acids in the form of polynucleotides or oligonucleotides can be used to focus treatment on a particular genetic target, either by interfering with its expression, or by restoring or augmenting its expression, or by editing the gene.

Delivering nucleic acids into cells or tissues presents challenges because nucleic acids are relatively large, negatively charged, hydrophilic compounds which are not capable of passively diffusing across the cell membrane and are also vulnerable to nucleases. (Akhtar, Basu S Fau-Wickstrom et al. 1991).

Existing approaches for delivering these nucleic acids across the cell membrane include viruses such as adeno-associated viruses as vectors for gene restoration, but these can cause immune responses in treated individuals (Mingozzi and High 2013). Ionizable lipids and polymers have also been used in experiments, but each has issues of transfection efficiency, stability and toxicity (Lv, Zhang et al. 2006). To increase the therapeutic activity of the nucleic acids, significant efforts in the field have focused on lipid nanoparticles (LNP) that comprise ionizable lipids, including ionizable cationic lipids (also known as "ionizable lipids" or "cationic lipids") and PEGylated lipids, for the efficient encapsulation and delivery of nucleic acids to cells (Tam, Chen et al. 2013, Kauffman, Webber et al. 2015).

Lipid particles have been engineered to obtain different pharmacokinetics, different bio-distribution in tissues, biodegradability, or altered toxicity, to favor the therapeutic activity of the nucleic acid.

The generation of iPSCs or iPSC-like cells involves the introduction of key reprogramming factors into somatic cells of donors or patients. Once stable iPSC clones are successfully established, they have the potential to be differentiated into most cell types for research or clinical applications. The advent of iPSC innovation offers unprecedented possibilities to the fields of disease modelling, drug discovery and cell-based therapeutics, as a versatile, physiologically-relevant in vitro system. The advantages of iPSC technology are of particular relevance in the field of neuroscience, wherein experimental models using primary tissues are not feasible and small animal models do not adequately mirror the complex human neuroanatomy.

iPSC-derived neurons show many morphological, biochemical and functional similarities to primary neurons. However, terminally differentiated cells including but not limited to neuronal cells are usually difficult to transfect while preserving their viability due to their sensitivity and inability to proliferate. Current methods, such as electroporation, calcium phosphate co-precipitation, lipofection and nucleofection often result in a high rate of cell mortality despite the fact that transfection and reprogrammed cells have been found to be clinically relevant and have applications in neurodegenerative disorders, CNS disorders and stem cell transplants For this reason, researchers and those interested in gene therapies to find suitable alternatives to nucleic acid delivery into cells.

SUMMARY OF THE INVENTION

According to the invention, there is provided a transfection reagent composition including Mol % of an ionizable lipid, or a pharmaceutically acceptable salt thereof; 15 to 25 Mol % structural lipid; 35 to 41 Mol % sterol; and 0.5 to about 10 Mol % of a stabilizing agent. In some embodiments, the ionizable lipid is an amino lipid or a pharmaceutically acceptable salt thereof. In some embodiments, the stabilizing agent includes more than one surfactant. In some embodiments the stabilizing agent is a polysorbate, such as polysorbate (80), or a mixture of polysorbates. In some embodiments the stabilizing agent is a maltoside. In some embodiments, the stabilizing agent is a mixture of polysorbate and maltoside. In a preferred embodiment, the stabilizing agent is a mixture of polysorbate 80, polysorbate 20, and Tridecyl-D-maltoside. The ratio of the three components is equal in one embodiment (1 to 1 to 1). In embodiments, the ionizable lipid includes about 40 Mol % of the composition. In embodiments, the stabilizing agent is about 0.5 to 5 Mol % of the composition. In some embodiments the sterol is cholesterol. According to the invention, there is provided the compositions described above, further comprising a nucleic acid or a peptide. In embodiments, the nucleic acid is a DNA, an RNA, or a plasmid capable of expressing an RNA. In some embodiments, the ionizable lipid is selected from BOCHD-C3-DMA, KC2, MC3, α-D-Tocopherolsuccinoyl and DODMA, In embodiments, the ionizable lipid is in the form of a pharmaceutically acceptable salt thereof. In embodiments, the structural lipid is 1,2-dioleoyl-sn-glycero-3-phosphoethanolamine (DOPE), and in others, DSPE or DSPC. In some embodiments, the compositions are in the form of lipid nanoparticles having a diameter of from about 15 nm to about 300 nm.

According to an embodiment of the invention, there is provided a method for transfecting an iPSC or iPSC-like cell with a nucleic acid therapeutic while maintaining activity of the nucleic acid and viability of the cell, by contacting the cell with the compositions described above.

According to another embodiment of the invention, there is provided a method for transfecting a neuronal cell with a nucleic acid therapeutic while maintaining activity of the nucleic acid and viability of the cell, by contacting the cell with the compositions described above. In embodiments, the cell is a mammalian cell. In some embodiments, the cell is human or obtained from a human.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention.

Figure 2:
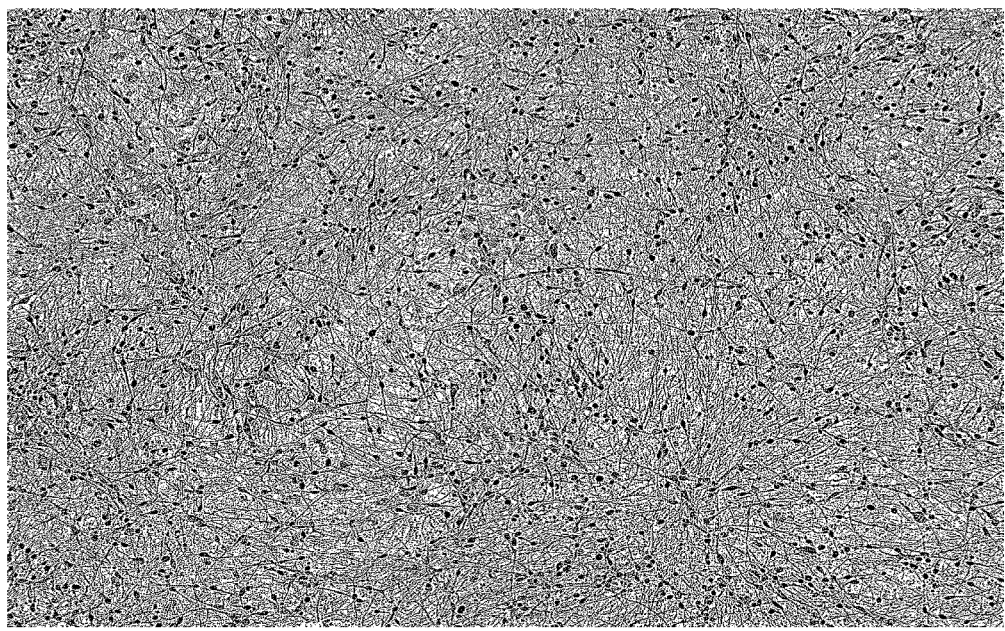
Figure 3A:
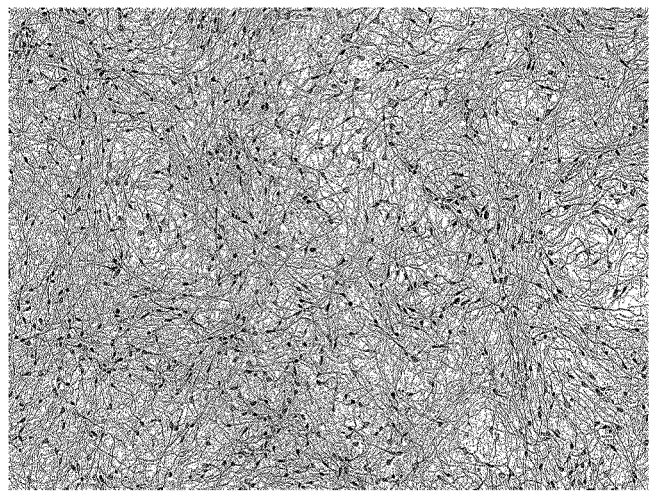
Figure 3B:
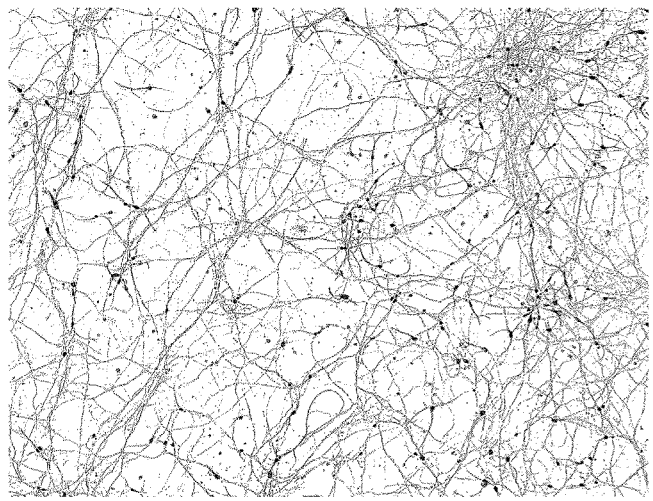
Figure 3C:
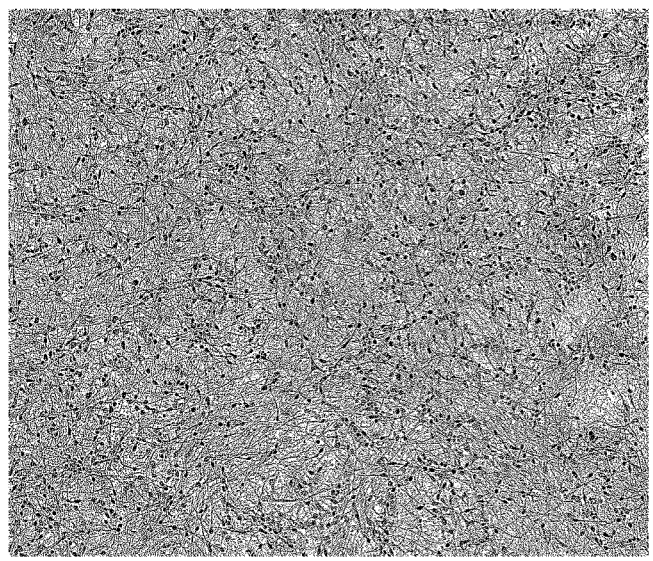
Figure 4A:
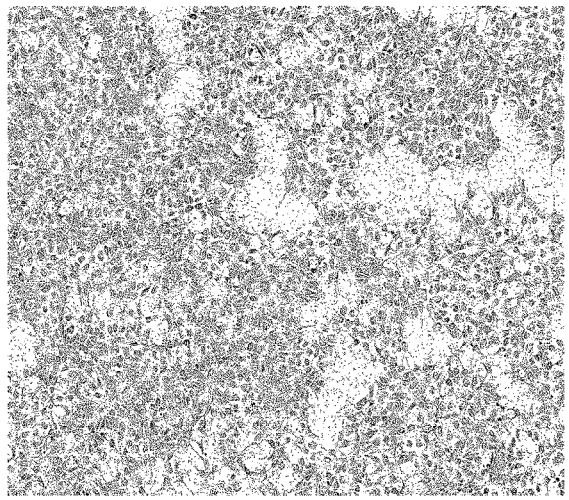
Figure 4B:
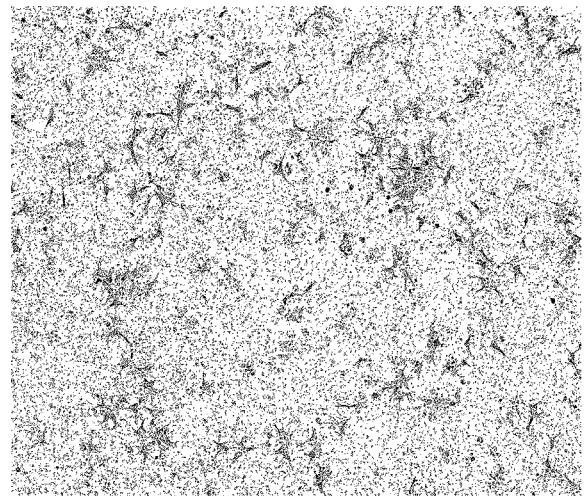
Figure 4C:
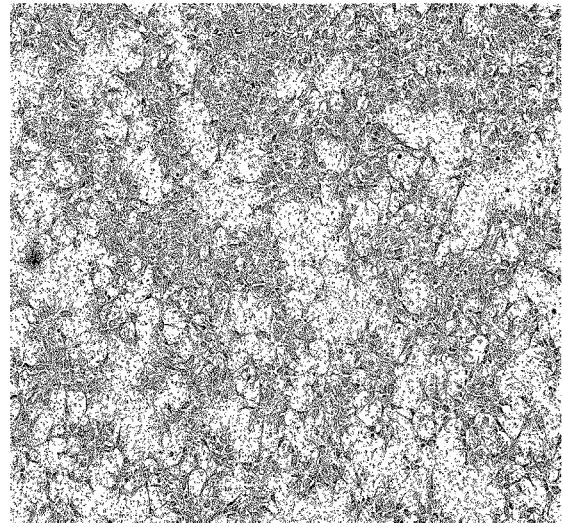
Figure 4D:
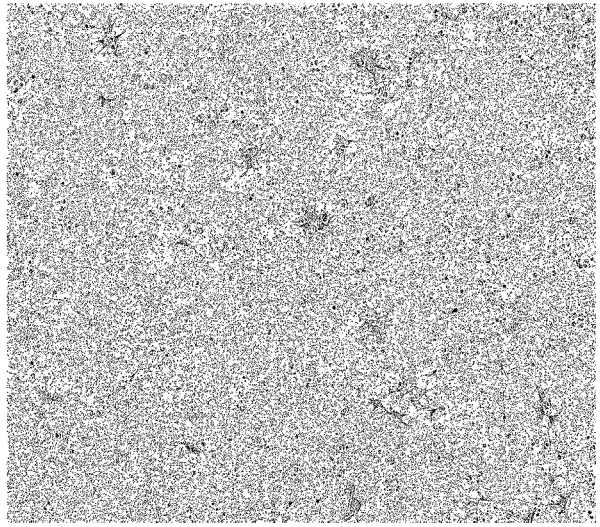
Figure 5:
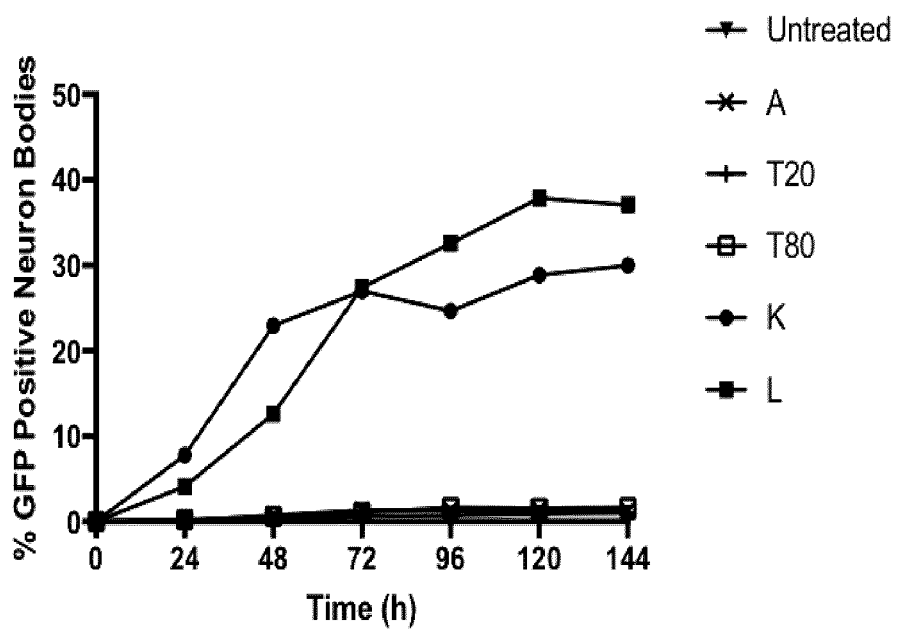
Figure 6:
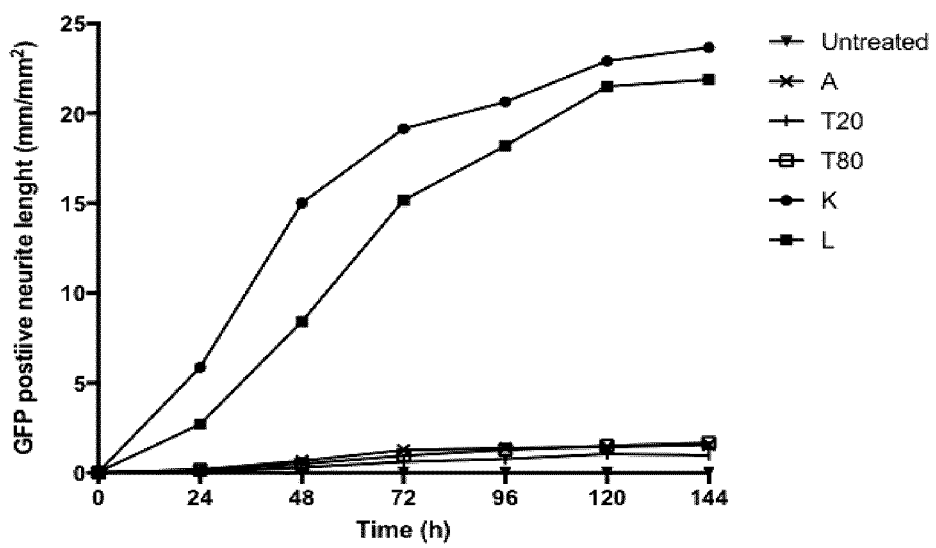
Figure 7:
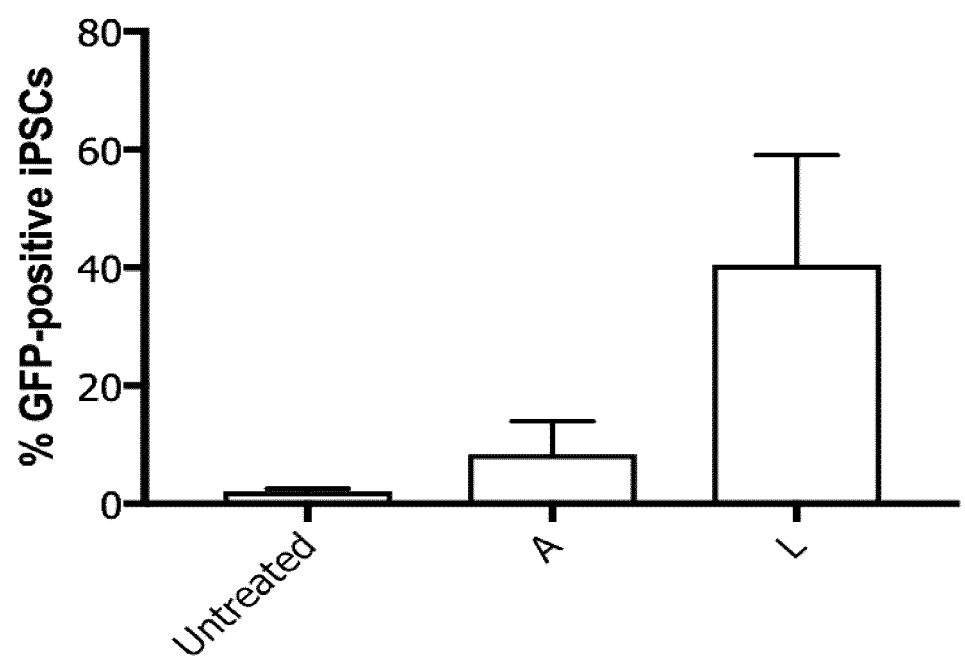
Figure 8A:
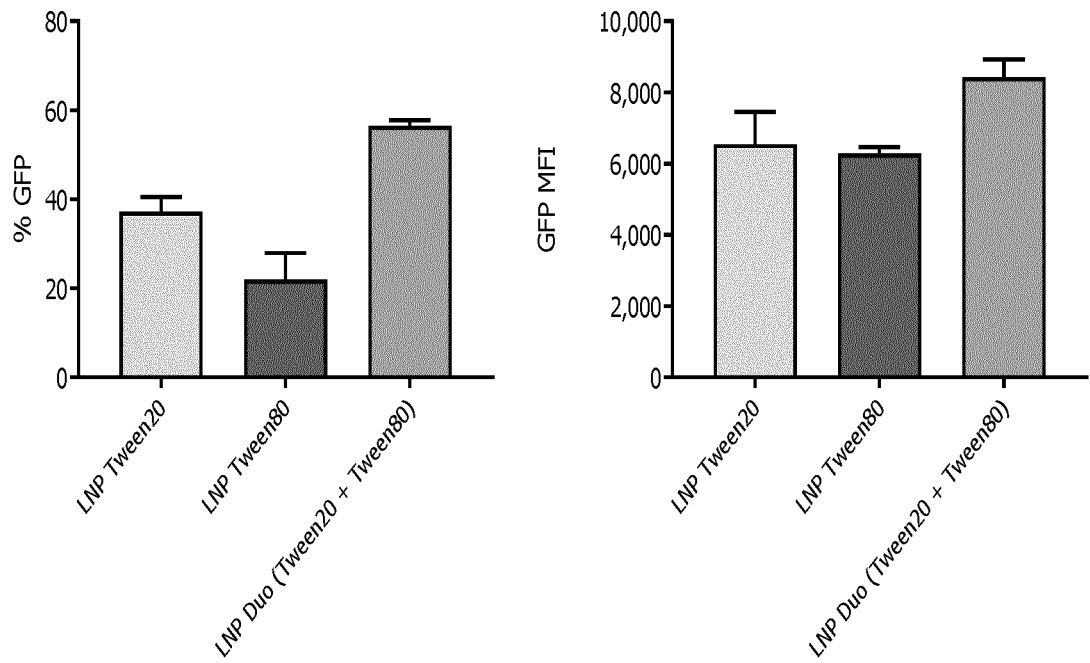
Figure 8B:
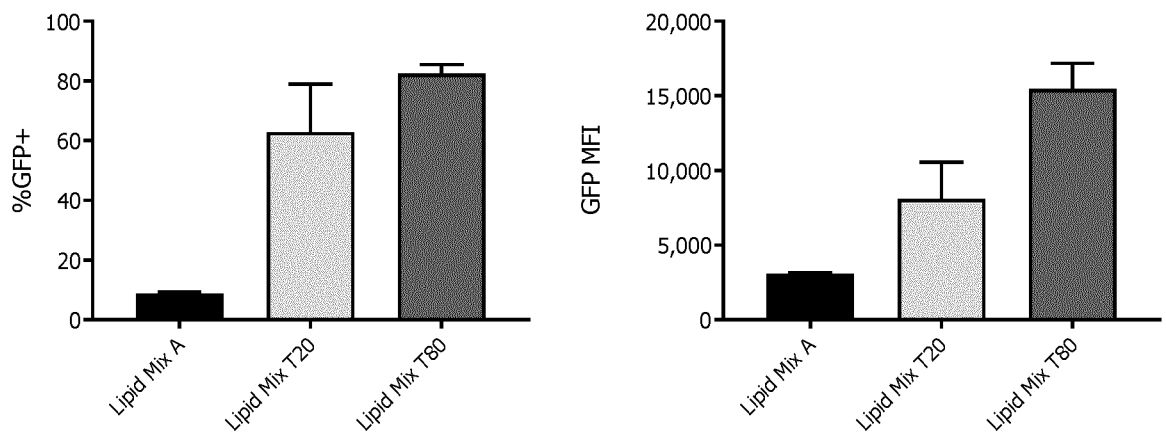
Figure 9A:
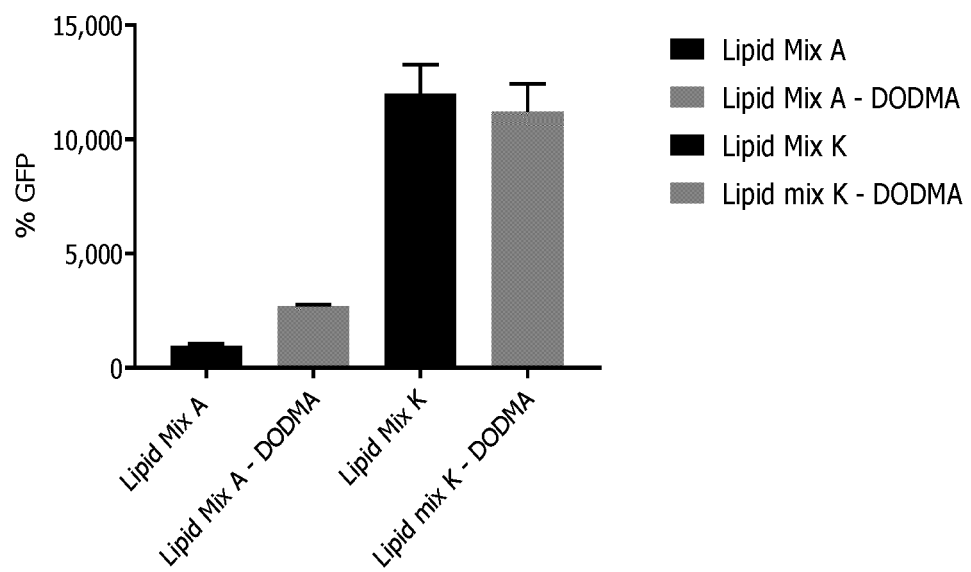
Figure 9B:
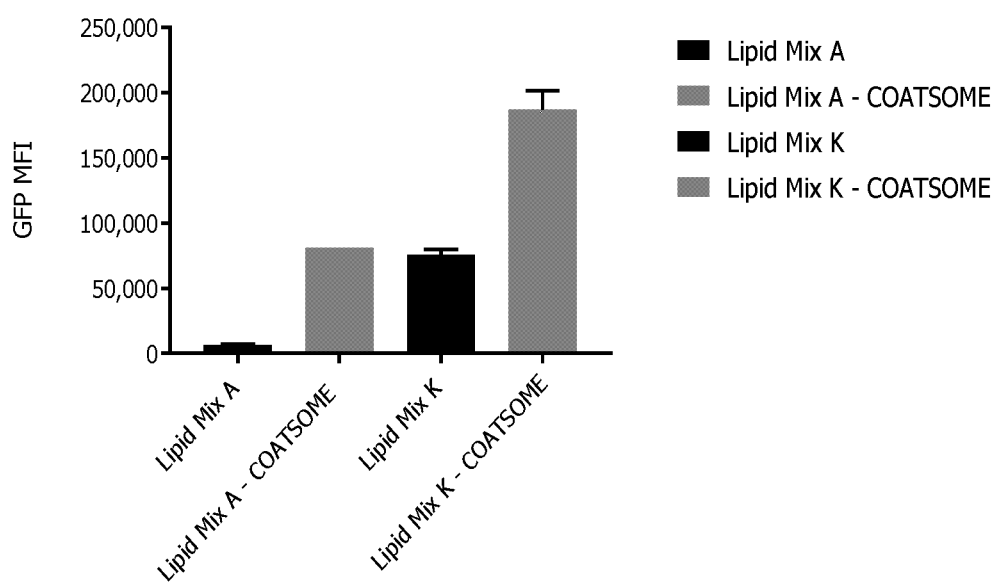
Figure 10:
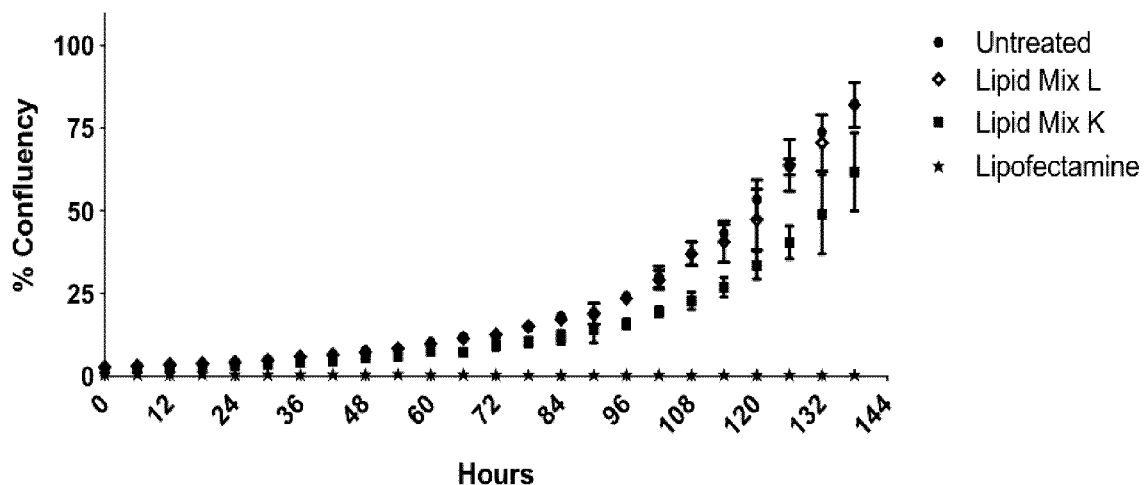
Figure 11:
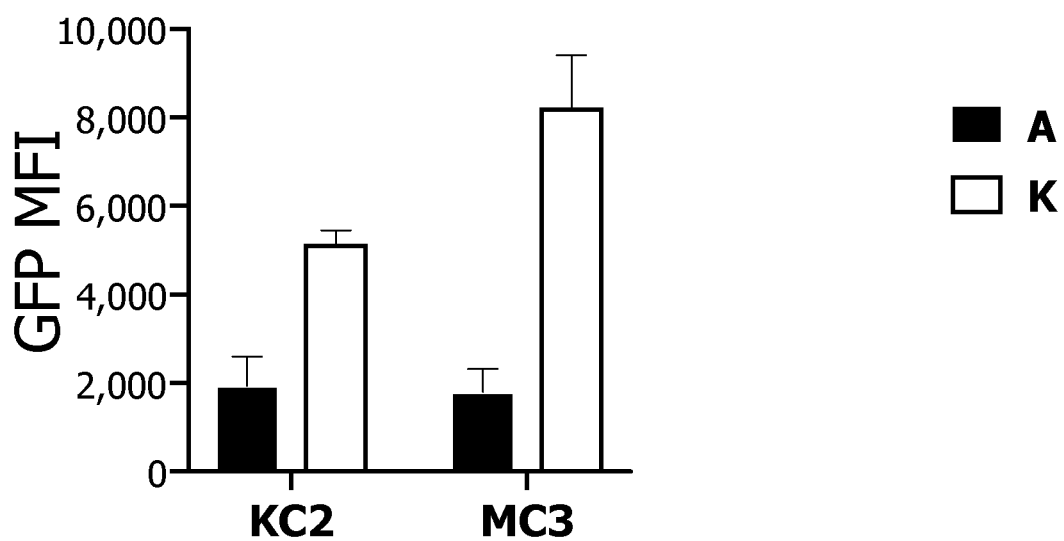

nucleic acid (P), ratio 4) were imaged at 72 hours post transfection. The long, string-like projections are neurites (axons and dendrites), and the bulbous elements are cell bodies (soma);

FIG. 2 is a black and white negative phase contrast microscopy image of mature neurons at DIV 14, taken with the Incucyte™ S3 Instrument, and are representative of those used in the studies;

FIGS. 3A-3C are representative phase contrast black and white negative images of iPSC-derived neurons taken with the Incucyte™ instrument, at DIV 14, untreated (3A) and at 48 hours following treatment with plasmid GFP-LNP prepared using LIPID MIXA (3B), or plasmid GFP-LNP prepared using LIPID MIX L (3C);

FIGS. 4A-4D are black and white negative phase contrast images of iPSC-derived neural progenitor cells, as taken with the Incucyte™ S3 instrument at day 4, untreated (4A), and at 48 hours following treatment with lipid particles consisting of LIPID MIX A at N/P 6 (4B), LIPID MIX L at N/P 6 (4C) or Lipofectamine™ (4D), containing plasmid encoding GFP;

FIG. 5 is a graph of the percentage of iPSC-derived neurons expressing GFP at DIV 14, from images captured at 0 to 144 hours post treatment with plasmid GFP-LNP (N/P 4) prepared using LIPID MIX A, LIPID MIX T20, LIPID MIX T80, LIPID MIX K, or LIPID MIX L;

FIG. 6 is a graph showing the length of GFP expressing neurites, per mm$^2$ of the image captured, in IPSC-derived neurons at DIV14 from 0 to 144 hours post treatment with plasmid GFP-LNP (N/P 4) prepared using LIPID MIX A, LIPID MIX T20, LIPID MIX T80, LIPID MIX K, or LIPID MIX L;

FIG. 7 is a bar graph showing the percentage of GFP-expressing iPSCs following no treatment, and treatment with mRNA-LNP (N/P 4) at concentration equivalent to 250 ng/mL prepared using Lipid Mix A and Lipid Mix L;

FIG. 8A is a bar graph showing effect of plasmid mediated expression of GFP in neural progenitor cells using LNP compositions with individual surfactants Tween 20 and Tween 80, and the surfactant combination of both Tween 20 and Tween 80;

FIG. 8B is a bar graph showing effect of plasmid mediated expression of GFP in neural progenitor cells using LNP compositions with individual surfactants Myrj52 (Lipid Mix A), Tween 20, and Tween 80;

FIG. 9A is a bar graph showing mRNA mediated expression of GFP (Mean Fluorescence Intensity) in neural progenitor cells using two similar LNP compositions but comprising two different ionizable lipids; and FIG. 9B is a bar graph showing mRNA mediated expression of GFP (Mean Fluorescence intensity) in neural progenitor cells using two similar LNP compositions comprising two different ionizable lipids;

FIG. 10 is a line graph comparing LNP treated NPC proliferation (confluence in dish) over 144 hours for untreated control, Lipid Mix L, Lipid Mix K, and Lipofectamine™ treated NPC; and FIG. 11 is a bar graph showing GFP levels in NPC measured by flow cytometry.

DETAILED DESCRIPTION

The present invention provides lipid mix compositions, their use in generating lipid based formulations of nucleic acid therapeutics and other oligomers such as peptides, and methods for using these lipid mixes and resulting formulations to overcome transfection-resistant cell types.

In another aspect, the lipid mix compositions of the invention are provided for mixing with nucleic acid therapeutics to create a lipid nucleic acid particle which enhances delivery of the nucleic acid into target cells or tissues, with less toxicity than more traditional lipid mix compositions or lipid nucleic acid particles such as those made from commercially available lipid mixes such as Lipofectamine™ transfecting agent.

In another aspect, the invention provides lipid mix compositions including ionizable lipid, one or more structural lipid(s), cholesterol, and a particular stabilizing mixture of detergents.

In another aspect, the lipid mix compositions according the invention are provided for formulating nucleic acid and peptide therapeutics for the treatment of diseases of the Central Nervous System, or for cell reprogramming, or for ex vivo transformation of patient cells "Lipid" refers to structurally diverse group of organic compounds that are fatty acid derivatives or sterols or could be lipid like materials as in lipidoids (example C12-200) and are characterized by being insoluble in water but soluble in many organic solvents.

"Lipid Particles". The invention provides lipid particles manufactured from the lipid mix compositions described above. The lipid particles contain a therapeutic agent in some embodiments. Lipid particles are assemblies of lipids, nucleic acid, cholesterol and stabilizing agents. Positive and negative charges, ratios, as well as hydrophilicity and hydrophobicity dictate the physical structure of the lipid particles in terms of size and orientation of components. The structural organization of these lipid particles may lead to an aqueous interior with a minimum bilayer as in liposomes or it could be containing a solid interior as in solid nucleic acid lipid nanoparticle.

"Ionizable lipid." The lipid particles include a ionizable lipid. As used herein, the term "ionizable lipid" refers to a lipid that is cationic or becomes ionizable (protonated) as the pH is lowered below the pK of the ionizable group of the lipid, but is progressively more neutral at higher pH values. At pH values below the pK, the lipid is then able to associate with negatively charged nucleic acids (e.g., oligonucleotides). As used herein, the term "ionizable lipid" includes zwitterionic lipids that assume a positive charge on pH decrease, and any of a number of lipid species that carry a net positive charge at a selective pH, such as physiological pH. Such lipids include, but are not limited to, N,N-dioleyl-N,N-dimethylammonium chloride (DODAC); 1,2-dioleoyl-3-dimethyaminopropane (DODAP), N-(2,3-dioleyloxy)propyl)-N,N,N-trimethylammonium chloride (DOTMA); N,N-distearyl-N,N-dimethylammonium bromide (DDAB); N-(2,3-dioleoyloxy)propyl)-N,N,N-trimethylammonium chloride (DOTAP); 3-(N—(N',N'-dimethylaminoethane)-carbamoyl) cholesterol (DC-Chol), and N-(1,2-dimyristyloxyprop-3-yl)-N,N-dimethyl-N-hydroxyethyl ammonium bromide (DMRIE).

"Viability" when referring to cells in vitro, means the ability to continue to grow, divide, and continue to grow and divide, as is normal for the cell type or tissue culture strain. Cell viability is affected by harsh conditions or treatments. Cell viability is not always important in nonclinical settings, but is critical in ex vivo therapy or parenteral administration.

In preferred embodiments, the ionizable lipid is an amino lipid. Suitable amino lipids useful in the invention include those described in WO 2009/096558, incorporated herein by reference in its entirety. Representative amino lipids include 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethyl-aminopropane chloride salt (DLin-TAP.Cl), 1,2-dilinoley-loxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), 2,2-dilinoleyl-4-dimethylaminomethyl-[1,3]-dioxolane (DLin-K-DMA). 1,2-dilinoleyloxy-N,N-dimethyl-3-amino-propane (DLin-DMA), heptatriaconta-6,9,28,31-tetraen-19-yl 4-(dimethylamino)butanoate (DLin-MC3-DMA), 2,2-dilinoleyl-4-(2-dimethylaminoethyl)-[1,3]-dioxolane (DLin-KC2-DMA), and 1,2-dioleyloxy-3-dimethylamino-propane (DODMA).

In other embodiments, newer ionizable lipids referred to in US20180000953 by Almarsson, Orn And Lawlor, Ciaran Patrick such as 3-(didodecylamino)-N1,N1,4-tridodecyl-1-piperazineethanamine (KL10), 14,25-ditridecyl-15,18,21,24-tetraaza-octatriacontane (KL25), 2-({8-[(3.beta.)-cholest-5-en-3-yloxy]octyl}oxy)-N,N-dimethyl-3-[(9Z,2Z)-octadeca-9,12-dien-1-yloxy]propan-1-amine (Octyl-CLin DMA), (2R)-2-({8-[(3.beta.)-cholest-5-en-3-yloxy] octyl}oxy)-N,N-dimethyl-3-[(9Z-,12Z)-octadeca-9,12-dien-1-yl oxy]propan-1-amine (Octyl-CLinDMA (2R)), and (2S)-2-({8-[.beta.)-cholest-5-en-3-yloxy]octyl}oxy)-N,N-dimethyl-3-[(9Z,1-2Z)-octadeca-9,12-dien-1-yl oxy] propan-1-amine (Octyl-CLinDMA (2S)) are employed.

In yet other embodiments, the ionizable lipid-like material is C12-200 as described by Kaufmann and his colleagues (Kaufmann k 2015):

phatidylethanolamines, diacylphosphatidylglycerols, ceramides, sphingomyelins, dihydrosphingomyelins, cephalins, and cerebrosides.

Exemplary structural lipids include zwitterionic lipids, for example, distearoylphosphatidylcholine (DSPC), dioleoylphosphatidylcholine (DOPC), dipalmitoylphosphatidylcholine (DPPC), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoyl-phosphatidyethanol amine (SOPE), and 1,2-dielaidoyl-sn-glycero-3-phophoethanolamine (transDOPE). In one preferred embodiment, the structural lipid is 1,2-dioleoyl-sn-glycero-3-phosphoethanolamine (DOPE).

In another embodiment, the structural lipid is any lipid that is negatively charged at physiological pH. These lipids include phosphatidylglycerols such as dioleoylphosphatidylglycerol (DOPG), dipalmitoylphosphatidylglycerol (DPPG), palmitoyloleoylphosphatidylglycerol (POPG), cardiolipin, phosphatidylinositol, diacylphosphatidylserine, diacylphosphatidic acid, and other anionic modifying groups joined to neutral lipids.

Other suitable structural lipids include glycolipids (e.g., monosialoganglioside $GM_1$).

Stabilizing Agents are included in lipid mix compositions and lipid nucleic acid embodiments to ensure integrity of the mixture among other actions. Stabilizing agents, in preferred embodiments of the invention, are detergents. Detergents are

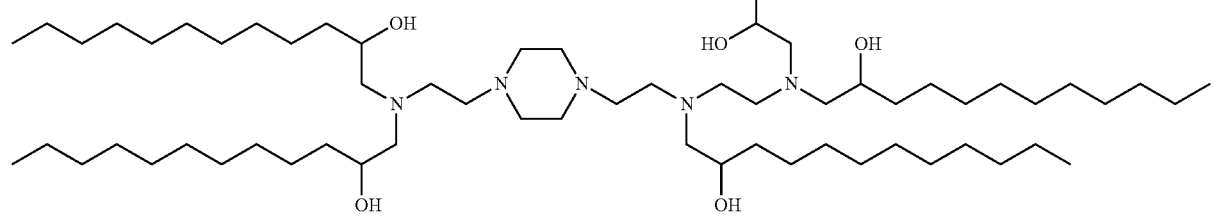

In preferred embodiments of the invention, the ionizable lipid is 1,17-bis(2-octylcyclopropyl)heptadecan-9-yl 4-(dimethylamino)butanoate hydrochloride (BOCHD-C3-DMA). This compound is disclosed in United States Published Application 2013323269.In other preferred embodiments, the ionizable lipid is COATSOME SS-E-P4C2. Cat No. SS-EC, or "α-D-Tocopherolsuccinoyl".

The ionizable lipid is present in embodiments of the composition and lipid particle of the invention preferably comprise an amount from about 35 to about 45 Mol %, or most preferably 40 Mol % ("Mol %" means the percentage of the total moles that is of a particular component).

Structural lipids. The composition and lipid particles of the invention include one or more structural lipids at about 20 Mol % of the composition. Suitable structural lipids support the formation of particles during manufacture. Structural lipids refer to any one of a number of lipid species that exist in either in an anionic, uncharged or neutral zwitterionic form at physiological pH. Representative structural lipids include diacylphosphatidylcholines, diacylphosa class of molecules which disrupt or help form the hydrophobic-hydrophilic interactions among molecules. Suitable detergents include polysorbate 20, (also known as Tween 20; polyoxyethylene sorbitan monolaurate; polyoxyethylene (20) sorbitan monolaurate, or IUPAC name 2-[2-[3,4-bis(2-hydroxyethoxy)oxolan-2-yl]-2-(2-hydroxyethoxy)ethoxy] ethyl dodecanoate); polysorbate 80 (also known as Tween 80, IUPAC name 2-[2-[3,4-bis(2-hydroxyethoxy)oxolan-2-yl]-2-(2-hydroxyethoxy)ethoxy]ethyl octadec-9-enoate), and maltosides, such as n-Decyl-β-D-maltopyranoside, n-Dodecyl-β-D-maltopyranoside, and 6-Cyclohexyl-1-hexyl-β-D-maltopyranoside.

In a preferred embodiment, the stabilizing agent is Polysorbate 20, Polysorbate 80, and Tridecyl β-D-maltoside combined. In some embodiments, these three components are combined in a 1:1:1 ratio by weight. In some embodiments, the combination of three detergents together comprises 0.5 to 10 Mol % of the overall lipid mixture. In some embodiments, the combination of three detergents together comprises 1 to 3 Mol % of the overall lipid mixture. In some embodiments, the combination of three detergents together comprises 0.5 to 2.5 Mol % of the overall lipid mixture.

Sterols are included in the preferred lipid mix compositions, and lipid particles made therefrom include sterols, such as cholesterol and phytosterol. In the lipid mixes of the invention, cholesterol is present at 30 to 50 Mol % of the final lipid mix in some embodiments. Alternately cholesterol is present at 35 to 41 Mol % of the final lipid mix. Cholesterol is present as 35.9, 37.5, 38, 39, and 39.4 Mol % in various preferred embodiments.

Peptides. The lipid mix compositions and lipid particles of the present invention are useful for the systemic or local delivery of peptides. As used herein, the term "therapeutic peptide" is meant to include any amino acid chain whose delivery into a cell causes a desirable effect. A peptide is a short chain of amino acids, two to 50 amino acids in length, as opposed to a protein which has a longer chain (50 amino acids or more), often with tertiary and/or quaternary structure. The amino acids in a peptide are connected to one another in a sequence by bonds called peptide bonds.

Nucleic Acids. The lipid mix compositions and lipid particles of the present invention are useful for the systemic or local delivery of nucleic acids. As used herein, the term "nucleic acid therapeutic" (NAT) is meant to include any oligonucleotide or polynucleotide whose delivery into a cell causes a desirable effect. Fragments containing up to 50 nucleotides are generally termed oligonucleotides, and longer fragments are called polynucleotides. In particular embodiments, oligonucleotides of the present invention are 20-50 nucleotides in length. Embodiments of the invention, oligonucleotides are 996 to 4500 nucleotides in length, as in the case of messenger RNA.

Currently, NATs are being actively pursued in an increasing number of pre-clinical and clinical studies. These NATs include deoxyribonucleic acid, complementary deoxyribonucleic acid, complete genes, ribonucleic acid, oligonucleotides and ribozymes for gene therapies targeting a variety of diseases, such as cancer, infectious diseases, genetic disorders and neurodegenerative diseases. As described herein, the nucleic acid therapeutic (NAT) is incorporated into the lipid particle during its formation.

The nucleic acid that is present in a lipid particle according to this invention includes any form of nucleic acid that is known. The nucleic acids used herein can be single-stranded DNA or RNA, or double-stranded DNA or RNA, or DNA-RNA hybrids. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include antisense oligonucleotides, ribozymes, microRNA, mRNA, and triplex-forming oligonucleotides.

Plasmid DNA is a preferred nucleic acid formulated in embodiments of the invention. A plasmid is a DNA molecule that is separate from chromosomal DNA in a cell, and can replicate independently. Plasmids range from less than 1000 nucleotides to tens of thousands of nucleotides in size. The most common form is small circular, double-stranded DNA. Plasmids can be synthesized and delivered to mammalian cells for therapeutic purposes. Synthetic plasmids are used as vectors in molecular cloning, serving to drive the replication of recombinant DNA sequences within host organisms.

Plasmids may be introduced into cells via transformation using physical methods such as electroporation, or chemical means as in the present invention, via lipid particle-enhanced transfection. These lipid-based vector systems have several advantages over physical techniques, which include: i) high biocompatibility and low toxicity in cell and tissue systems ii) relative ease of manufacture iii) lipophilic matrices are less susceptible to the erosion phenomena observed in polymeric systems iv) an increased circulatory half-life in vivo due to their invisibility from the immune system.

Thus, in one embodiment, the nucleic acid therapeutic (NAT) is a plasmid or circular nucleic acid construct. In another embodiment, the NAT is a replicon. In one embodiment, the NAT is an mRNA.

The term "nucleic acids" also refers to ribonucleotides, deoxynucleotides, modified ribonucleotides, modified deoxyribonucleotides, modified phosphate-sugar-backbone oligonucleotides, other nucleotides, nucleotide analogs, and combinations thereof, and can be single stranded, double stranded, or contain portions of both double stranded and single stranded sequence, as appropriate.

As used herein, the terms "polynucleotide" and "oligonucleotide" are used interchangeably and mean single-stranded and double-stranded polymers of nucleotide monomers, including 2'-deoxyribonucleotides (DNA) and ribonucleotides (RNA) linked by internucleotide phosphodiester bond linkages, e.g., 3'-5' and 2'-5', inverted linkages, e.g., 3'-3' and 5'-5', branched structures, or internucleotide analogs. Polynucleotides have associated counter ions, such as H+, NH4+, trialkylammonium, Mg2+, Na+, and the like. A polynucleotide may be composed entirely of deoxyribonucleotides, entirely of ribonucleotides, or chimeric mixtures thereof. Polynucleotides may be comprised of internucleotide, nucleobase and/or sugar analogs.

As used herein, "nucleic acid" is a nucleobase sequence-containing polymer, or polymer segment, having a backbone formed from nucleotides, or analogs thereof.

As used herein, "NIP" is the ratio of moles of the amine groups of ionizable lipids to those of the phosphate groups of mRNA/DNA. In embodiments of the invention, N/P ratios are from N/P 3 to N/P7, and most preferred ratios are from N/P4 to N/P 6.

The lipid particles according to some embodiments of the invention can be characterized by electron microscopy. The particles of the invention having a substantially solid core have an electron dense core as seen by electron microscopy. One such structure is disclosed in U.S. Pat. No. 9,758,795 by Cullis et al. Electron dense is defined such that area-averaged electron density of the interior 50% of the projected area of a solid core particle (as seen in a 2-D cryogenic EM image) is not less than x % (x=20%, 40%, 60%) of the maximum electron density at the periphery of the particle. Electron density is calculated as the absolute value of the difference in image intensity of the region of interest from the background intensity in a region containing no nanoparticle.

The lipid particles of the invention can be assessed for size using devices that size particles in solution, such as the Malvern™ Zetasizer™. The particles have a mean particle diameter of from about 15 nm to about 300 nm. Another term for lipid particle is "LNP", which stands for "lipid nanoparticles". In some embodiments, the mean particle diameter is greater than 300 nm. In some embodiments, the lipid particle has a diameter of about 300 nm or less, 250 nm or less, 200 nm or less, 150 nm or less, 100 nm or less, or 50 nm or less. In one embodiment, the lipid particle has a diameter of from about 50 to about 150 nm. Smaller particles generally exhibit increased circulatory lifetime in vivo compared to larger particles. In one embodiment, the lipid particle has a diameter from about 15 to about 50 nm.

Mixing. The lipid particles according to embodiments of the invention can be prepared by standard T-tube mixing techniques, turbulent mixing, trituration mixing, agitation promoting orders self-assembly, or passive mixing of all the elements with self-assembly of elements into nanoparticles. A variety of methods have been developed to formulate lipid nanoparticles (LNP) containing genetic drugs. Suitable methods are disclosed in U.S. Pat. No. 5,753,613 by Ansell, Mui and Hope and U.S. Pat. No. 6,734,171 by Saravolac et al., by way of example. These methods include mixing preformed lipid particles with nucleic acid therapeutic (NAT) in the presence of ethanol or mixing lipid dissolved in ethanol with an aqueous media containing NAT and result in lipid particles with NAT encapsulation efficiencies of 65-95%. Both of these methods rely on the presence of ionizable lipid to achieve encapsulation of NAT and a stabilizing agent to inhibit aggregation and the formation of large structures. The properties of the lipid particle systems produced, including size and NAT encapsulation efficiency, are sensitive to a variety of formulation parameters such as ionic strength, lipid and ethanol concentration, pH, NAT concentration and mixing rates. J Drug Target. 2016 November; 24(9):821-835.

Microfluidic two-phase droplet techniques have been applied to produce monodisperse polymeric microparticles for drug delivery or to produce large vesicles for the encapsulation of cells, proteins, or other biomolecules. The use of hydrodynamic flow focusing, a common microfluidic technique to provide rapid mixing of reagents, to create monodisperse liposomes of controlled size has been demonstrated.

In general, parameters such as the relative lipid and NAT concentrations at the time of mixing, as well as the mixing rates are difficult to control using current formulation procedures, resulting in variability in the characteristics of NAT produced, both within and between preparations. Automatic micro-mixing instruments such as the NanoAssemblr™ instruments (Precision NanoSystems Inc, Vancouver, Canada) enable the rapid and controlled manufacture of nanomedicines (liposomes, lipid nanoparticles, and polymeric nanoparticles). NanoAssemblr™ instruments accomplish controlled molecular self-assembly assembly of nanoparticles via microfluidic mixing cartridges that allow millisecond mixing of nanoparticle components at the nanoliter, microlitre, or larger scale with customization or parallelization. Rapid mixing on a small scale allows reproducible control over particle synthesis and quality that is not possible in larger instruments.

Preferred methods incorporate instruments such as the microfluidic mixing devices like the NanoAssemblr™ Spark™, Ingnite™, Benchtop™ and Blaze™ in order to achieve nearly 100% of the nucleic acid used in the formation process is encapsulated in the particles in one step. In one embodiment, the lipid particles are prepared by a process by which from about 90 to about 95% of the nucleic acid used in the formation process is encapsulated in the particles.

U.S. Pat. Nos. 9,758,795 and 9,943,846, by Cullis et al. describe methods of using small volume mixing technology and novel formulations derived thereby. U.S. Application Pub. No. 20160022580 by Ramsay et al. describes more advanced methods of using small volume mixing technology and products to formulate different materials. U.S. Application Pub. No. 2016235688 by Walsh, et al. discloses microfluidic mixers with different paths and wells to elements to be mixed. PCT Publication WO2017117647 by Wild, Leaver and Taylor discloses microfluidic mixers with disposable sterile paths. PCT Publication No WO201711764 by Wild, Leaver and Taylor discloses bifurcating toroidal micromixing geometries and their application to micromixing. PCT Publication No. WO2018006166 by Chang, Klaassen, Leaver et al. disclose a programmable automated micromixer and mixing chips therefor. U.S. Design Nos. D771834, D771833, D772427, and D803416, by Wild and Weaver, and D800335, D800336 and D812242 by Chang et al. disclose mixing cartridges having microchannels and mixing geometries for mixer instruments sold by Precision NanoSystems Inc.

In embodiments of the invention, devices for biological microfluidic mixing are used to prepare the lipid particles and therapeutic formulations of the invention. The devices include a first and second stream of reagents, which feed into the microfluidic mixer, and lipid particles are collected from the outlet, or in other embodiments, emerge into a sterile environment.

The first stream includes a therapeutic agent in a first solvent. Suitable first solvents include solvents in which the therapeutic agents are soluble and that are miscible with the second solvent. Suitable first solvents include aqueous buffers. Representative first solvents include citrate and acetate buffers.

The second stream includes lipid mix materials in a second solvent. Suitable second solvents include solvents in which the ionizable lipids are soluble and that are miscible with the first solvent. Suitable second solvents include 1,4-dioxane, tetrahydrofuran, acetone, acetonitrile, dimethyl sulfoxide, dimethylformamide, acids, and alcohols. Representative second solvents include aqueous ethanol 90%, or anhydrous ethanol.

In one embodiment of the invention, a suitable device includes one or more microchannels (i.e., a channel having its greatest dimension less than 1 millimeter). In one example, the microchannel has a diameter from about 20 to about 300 µm. In examples, at least one region of the microchannel has a principal flow direction and one or more surfaces having at least one groove or protrusion defined therein, the groove or protrusion having an orientation that forms an angle with the principal direction (e.g., a staggered herringbone mixer), as described in United States Patent Pub. No. 20040262223, or a bifurcating toroidal flow as described in United States Patent Pub. No. 2018093232. To achieve maximal mixing rates, it is advantageous to avoid undue fluidic resistance prior to the mixing region. Thus, one example of a device has non-microfluidic channels having dimensions greater than 1000 microns, to deliver the fluids to a single mixing channel.

Less automated micromixing methods and instruments such as those disclosed in Zhang, S., et al; Chem. Eng. J.; 144; 2008; 324-328 and Strook A., et al; Science 295; 2002; 647-651 are also useful in creating formulations of the invention. More primitive systems involving T-tube mixing are disclosed in Jeffs L B et al., A scalable, extrusion-free method for efficient liposomal encapsulation of plasmid DNA. Pharm Res. 2005; 22(3):362-72.

The lipid particles of the present invention may be used to deliver a therapeutic agent to a cell, in vitro or in vivo. In particular embodiments, the therapeutic agent is a nucleic acid, which is delivered to a cell using nucleic acid-lipid particles of the present invention. The nucleic acid can be an siRNA, miRNA, a LNA, a plasmid or replicon, an mRNA, a single gene. In other embodiments, the therapeutic agent is a peptide, which is delivered to a cell using peptide-lipid particles of the present invention. The methods and lipid mix compositions may be readily adapted for the delivery of any suitable therapeutic agent for the treatment of any disease or disorder that would benefit from such treatment.

In certain embodiments, the present invention provides methods for introducing a nucleic acid into a cell (i.e. transfection). Transfection is a technique commonly used in molecular biology for the introduction of nucleic acid therapeutics (or NATs) from the extracellular to the intracellular space for the purpose of transcription, translation and expression of the delivered gene(s). Transfection efficiency is commonly defined as either the i) percentage of cells in the total treated population showing positive expression of the delivered gene, as measured by protein quantification methods such as live cell imaging (for detection of fluorescent protein), flow cytometry or ELISA, or ii) the intensity or amount of protein expressed by treated cell(s). These methods may be carried out by contacting the particles or lipid mix compositions of the present invention with the cells for a period of time sufficient for intracellular delivery to occur.

Typical applications include using well known procedures to provide intracellular delivery of siRNA to knock down or silence specific cellular targets. Alternatively, applications include delivery of DNA or mRNA sequences that code for therapeutically useful polypeptides. In this manner, therapy is provided for genetic diseases by supplying deficient or absent gene products. Methods of the present invention may be practiced in vitro, ex vivo, or in vivo. For example, the lipid mix compositions of the present invention can also be used for delivery of nucleic acids to cells in vivo, using methods which are known to those of skill in the art. In another example, the lipid mix compositions of the invention can be used for delivery of nucleic acids to a sample of patient cells that are ex vivo, then are returned to the patient.

The delivery of nucleic acid therapeutics by a lipid particle of the invention is described below.

For in vivo administration, the pharmaceutical compositions are preferably administered parenterally (e.g., intraarticularly, intravenously, intraperitoneally, subcutaneously, intrathecally, intradermaly, intratrachealy, intraosseous or intramuscularly). In particular embodiments, the pharmaceutical compositions are administered intravenously, intrathecally, or intraperitoneally by a bolus injection. Other routes of administration include topical (skin, eyes, mucus membranes), oral, pulmonary, intranasal, sublingual, rectal, and vaginal.

For ex vivo applications, the pharmaceutical compositions are preferably administered to biological samples that have been removed from the organism, then the cells are washed and restored to the organism. The organism may be a mammal, and in particular may be human. This process is used for cell reprogramming, genetic restoration, immunotherapy, for example.

In one embodiment, the present invention provides a method of modulating the expression of a target polynucleotide or polypeptide. These methods generally comprise contacting a cell with a lipid particle of the present invention that is associated with a nucleic acid capable of modulating the expression of a target polynucleotide or polypeptide. As used herein, the term "modulating" refers to altering the expression of a target polynucleotide or polypeptide. Modulating can mean increasing or enhancing, or it can mean decreasing or reducing.

In related embodiments, the present invention provides a method of treating a disease or disorder characterized by overexpression of a polypeptide in a subject, comprising providing to the subject a pharmaceutical composition of the present invention, wherein the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof.

In related embodiments, the present invention provides a method of treating a disease or disorder characterized by under-expression of a polypeptide in a subject, comprising providing to the subject a pharmaceutical composition of the present invention, wherein the therapeutic agent is selected from an mRNA, a self amplifying RNA (SAM), a self-replicating DNA, or a plasmid, comprises a nucleic acid therapeutic that specifically encodes or expresses the under-expressed polypeptide, or a complement thereof.

In embodiments, formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient may generally be equal to the dosage of the active ingredient which would be administered to a subject and/or a convenient fraction of such a dosage including, but not limited to, one-half or one-third of such a dosage.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1 percent and 99 percent (w/w) of the active ingredient.

Pharmaceutical formulations may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams and Wilkins, Baltimore, Md., 2006; incorporated herein by reference in its entirety). The use of a conventional excipient medium is contemplated herein, except insofar as any conventional excipient medium may be incompatible with a substance or its derivatives, such as by producing any undesirable biological effect or otherwise interacting in a deleterious manner with any other component(s) of the pharmaceutical composition.

In some embodiments, the particle size of the lipid particles may be increased and/or decreased. The change in particle size may be able to help counter biological reaction such as, but not limited to, inflammation or may increase the biological effect of the NAT delivered to mammals by changing biodistribution.

Pharmaceutically acceptable excipients used in the manufacture of pharmaceutical compositions include, but are not limited to, inert diluents, surface active agents and/or emulsifiers, preservatives, buffering agents, lubricating agents, and/or oils. Such excipients may optionally be included in the pharmaceutical formulations of the invention.

In some embodiments, exemplary plasmid or other NAT encodes the protein or enzyme selected from human growth hormone, erythropoietin, a 1-antitrypsin, acid alpha glucosidase, arylsulfatase A, carboxypeptidase N, a-galactosidase A, alpha-L-iduronidase, iduronate-2-sulfatase, iduronate sulfatase, N-acetylglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, glucocerebrosidase, heparan sulfamidase, heparin-N-sulfatase, lysosomal acid lipase, hyaluronidase, galactocerebrosidase, ornithine transcarbamylase (OTC), carbamoyl-phosphate synthetase 1 (CPS 1), argininosuccinate synthetase (ASS 1), argininosuccinate lyase (ASL), arginase 1 (ARGI), cystic fibrosis transmembrane conductance regulator (CFTR), survival motor neuron (SMN), Factor VIII, Factor IX, meganucleases like TALENS, Cas9 and self-replicating RNA's and low density lipoprotein receptors (LDLR).

Other plasmid or nucleic acids can be applied to cell-based system using this invention in the context of a research or screening platform. These include the introduction of genetic material for the purpose of inducing specific physiological or functional changes in cells, such as in the process of reprogramming for the generation of induced pluripotent stem cells. In this case, specific genes (known as Yamanaka factors) are introduced to patient-derived somatic cells, which trigger a reversal of the cell to a stem cell-like state. These enable the cells to divide indefinitely and become pluripotent (able to differentiate to many other downstream cell types) which can be used for both research and clinical applications. These and similar genetic manipulation steps can be enhanced by the lipid particles of the invention to improve the efficiency of processes commonly used when working with induced stem cells.

The following is a description of representative lipid particles prepared with nucleic acid (LNP), how they are made, evidence of their advantages, and methods for using them to deliver therapeutic benefits.

Formulation of Lipid particles was performed by rapidly mixing a lipid-ethanol solution with an aqueous buffer inside a microfluidic mixer designed to induce chaotic advection and provide a controlled mixing environment at intermediate Reynolds number (24<Re<1000). The microfluidic channels have herringbone features or are configured in a manner as shown in PCT Publication WO2017117647. In other embodiments, the microfluidic channels are structured as in U.S. Pat. No. 10,076,730.

Particle sizes and "polydispersity index" (PDI) of the Lipid particle were measured by dynamic light scattering (DLS). PDI indicates the width of the particle distribution. This is a parameter calculated from a cumulative analysis of the (DLS)-measured intensity autocorrelation function assuming a single particle size mode and a single exponential fit to the autocorrelation function. From a biophysical point of view, a PDI below 0.1 indicates that the sample is monodisperse. The particles produced by mechanical micromixers such as the NanoAssemblr™ Spark and Benchtop are substantially homogeneous in size assuming all other variables are neutral. A lower PDI indicates a more homogenous population of lipid particles.

In certain embodiments, a stabilizing agent is present in the particle in an amount from about 0.5 to about 10 Mol %. In some embodiments, the stabilizing agent is a mixture of detergents such as Polysorbates and maltosides.

In embodiments, the stabilizing agent is present in the lipid based formulation at about 2.5 Mol %.

In a preferred embodiment, the stabilizing agent is a mixture of Polysorbate 20 (polysorbate 20 or Polyoxyethylene (20) sorbitan monolaurate), Polysorbate 80 (polysorbate 80 or polyoxyethylene (20) sorbitan monooleate, and Tridecyl β-D-maltoside. In a preferred embodiment, these three components are present in a substantially 1:1:1 wt/wt ratio, or for clarity, about 33.33% each component.

In preferred embodiments, the nucleic acid is a plasmid composed of double stranded deoxyribonucleic acid. A plasmid is a genetic structure that resides in a cell's cytoplasm (as opposed to the nucleic where the traditional cellular genetics reside) cell that can replicate independently of the chromosomes, typically a small circular DNA strand. This is not a normal mammalian genetic construct but is used as a therapeutic option for manipulating the genetic function in a cell. Plasmids can also be used to create novel cellular or animal models for medical research. Plasmids are an important tool in molecular biology and as an emerging therapeutic due to their i) ease of manipulation and isolation ii) ability to self-replicate for scaled-up manufacturing iii) long term stability iv) functionality in a range of organisms and applications. An engineered plasmid will have, in addition to a replication origin (or not, depending on the intended use), restriction enzyme recognition sites to allow breaking the circle to introduce new genetic material, and a selective marker such as an antibiotic resistance gene. A plasmid may be from about 1000 base pairs to about 20 kilobase pairs.

Terminology

As used herein, the term "about" is defined as meaning 10% plus or minus the recited number. It is used to signify that the desired target concentration might be, for example, 40 Mol %, but that through mixing inconsistencies, the actual percentage might differ by +/−5 Mol %.

As used herein, the term "substantially" is defined as being 5% plus or minus the recited number. It is used to signify that the desired target concentration might be, for example, 40 Mol %, but that through mixing inconsistencies, the actual percentage might differ by +/−5 Mol %.

As used herein, the term "nucleic acid" is defined as a substance intended to have a direct effect in the diagnosis, cure, mitigation, treatment or prevention of disease, or to have direct effect in restoring, correcting or modifying physiological functions, or to act as a research reagent. In preferred embodiments, the nucleic acid is an oligonucleotide. In preferred embodiments, the therapeutic agent is a nucleic acid therapeutic, such as an RNA polynucleotide. In preferred embodiments, the therapeutic agent is double stranded circular DNA (plasmid).

As used herein, the term "reagent" is defined by the fact that it has a direct influence on the biological effect of cells, tissues or organs. Reagents include but are not limited polynucleotides, proteins, peptides, polysaccharides, inorganic ions and radionuclides. Examples of nucleic acid reagents include but are not limited to antisense oligonucleotides, ribozymes, microRNA, mRNA, ribozyme, tRNA, tracrRNA, sgRNA, snRNA, siRNA, shRNA, ncRNA, miRNA, mRNA, pre-condensed DNA, pDNA or an aptamer. Nucleic Acid Reagents are used to silence genes (with for example siRNA), express genes (with for example mRNA), edit genomes (with for example CRISPR/Cas9), and reprogram cells for return to the originating organism (for example ex vivo cell therapy to reprogram immune cells for cancer therapy). "Reagent" includes ancillary agents in cell therapy applications, and pharmaceuticals.

In this disclosure, the word "comprising" is used in a non-limiting sense to mean that items following the word are included, but items not specifically mentioned are not excluded. It will be understood that in embodiments which comprise or may comprise a specified feature or variable or parameter, alternative embodiments may consist, or consist essentially of such features, or variables or parameters. A reference to an element by the indefinite article "a" does not exclude the possibility that more than one of the elements is present, unless the context clearly requires that there be one and only one of the elements.

In this disclosure, "transfecting reagent" means a composition that enhances the transfer of nucleic acid into cells for the purpose of inducing the expression of a specific gene(s) of interest. It typically includes a ionizable lipid to associate with nucleic acid, and structural lipids. LIPOFECTIN™ and LIPOFECTAMINE™ are established commercial transfecting reagents sold by ThermoFisher Scientific.

In this disclosure the recitation of numerical ranges by endpoints includes all numbers subsumed within that range including all whole numbers, all integers and all fractional intermediates (e.g., 1 to 5 includes 1, 1.5, 2, 2.75, 3, 3.80, 4, and 5 etc.). In this disclosure the singular forms an "an" and "the" include plural referents unless the content clearly dictates otherwise. Thus, for example, reference to a composition containing "a compound" includes a mixture of two or more compounds. In this disclosure term "or" is generally employed in its sense including "and/or" unless the content clearly dictates otherwise.

The following examples are provided for the purpose of illustrating, not limiting, the invention.

EXAMPLES

Materials and Methods

Some of the Lipid Mixes were formed with 1,17-bis(2-octylcyclopropyl)heptadecan-9-yl 4-(dimethylamino) butanoate (BOCHD-C3-DMA) was synthesized by Avanti Polar Lipids (Alabaster, Ala., USA). Other Lipid Mixes were formed with DODMA (also Avanti Polar Lipids) or COATSOME™ SS-E-P4C2. Cat No. SS-33/4PE-15 (NOF America Corporation, Irvine, Calif.).

Structural lipid 1,2-dioleoyl-sn-glycero-3-phosphoethanolamine (DOPE) was also obtained from Avanti Lipids. Kc2 and Dlin-MC3-DMA were synthesized in house. Salts and reagents not otherwise described with respect to source were obtained from Fisher Scientific (Fair Lawn, N.J.). Control and Lipofectamine™ control were the exceptions. According to Wikipedia, Lipofectamine™ agent is described in U.S. Pat. No. 7,479,573 by Yongliang, Chu et al. and has a composition of 3:1 w/w DOSPA:DOPE.

RNase A was obtained from Applied Biosystems/Ambion (Austin, Tex.).

Stabilizing agent (TW20:TW80:TBD) is meant to mean a mixture of polysorbate 20 (also known as polyethylene (20) sorbitan monolaurate or Tween™ 20), polysorbate (80)(also known as Polyethylene (80) sorbitan monooleate or Tween™80), and Tridecyl β-D-maltoside (all from Millipore Sigma, Burlington, Mass.) in a 1:1:1 wt/wt ratio. In other embodiments, polysorbate 80, or polysorbate 20, or maltoside are each present as stabilizing agent alone. In other embodiments they are in different ratios but still present together. In other embodiments only polysorbate 80 and maltoside comprise the stabilizing agent.

DiD means 'DiD'; DilC18(5) oil (1,1'-Dioctadecyl-3,3,3',3'-Tetramethylindodicarbocyanine Perchlorate) (Invitrogen D-307) and is a lipid label (remaining with the lipid) for research. Other such lipid dyes are dansyl DOPE and Fluorescein DHPE.

Oligonucleotide or polynucleotide (plasmid, or messenger RNA, hereinafter referred to as "nucleic acid" or "nucleic acid therapeutic") solution was prepared in 25 mM-100 mM acetate buffer at pH 4.0. Depending on the desired oligonucleotide-to-lipid ratio and formulation concentration, solutions were prepared at a target concentration of 2.3 mg/ml to 4 mg/ml total lipid. A lipid solution containing 1,17-bis(2-octylcyclopropyl)heptadecan-9-yl 4-(dimethylamino)butanoate hydrochloride, DOPE, cholesterol, 2.5 Mol % stabilizing agent, and 0-10%, DiD label, was prepared in ethanol and mixed with the nucleic acid to achieve an ethanol concentration of 25% (v/v). For certain examples, heptatriaconta-6,9,28,31-tetraen-19-yl 4-(dimethylamino)butanoate (DLin-MC3-DMA), DODMA, or 2,2-dilinoleyl-4-(2-dimethylaminoethyl)-[1,3]-dioxolane (DLin-KC2-DMA) was used in place of 1,17-bis(2-octylcyclopropyl)heptadecan-9-yl 4-(dimethylamino)butanoate hydrochloride (BOCHD-C3-DMA).

Nucleic acid to formulation ratios were N/P 4 to N/P 6, wherein "N" is the number of moles of the lipid amine and "P" is the number of moles of the nucleotide phosphate (each nucleotide phosphate unit is considered as 1 mole unit), and "4" and "6" are the ratios thereof.

Lipid particles were prepared by standard microfluidic processes described above under "Mixing", by using the NanoAssemblr™ Benchtop or NanoAssemblr™ Spark. In this way, mixing occurred by chaotic advection, causing the separation of laminate streams to become increasingly small, thereby promoting rapid diffusion. This mixing occurs on a millisecond time scale and results in the lipids being transferred to a progressively more aqueous environment, reducing their solubility and resulting in the spontaneous formation of lipid nanoparticles (LNP). Entrapment of plasmid occurs obtained through association of the positively charged lipid head group and negatively charged oligonucleotide.

Induced pluripotent stem cells or iPSC

Induced pluripotent stem cells (iPSCs) were generated from reprogrammed donor-derived fibroblasts using non-integrating oriP/EBNA1 plasmids. Cells were maintained on Corning® Growth Factor Reduced (GFR) Basement Membrane Matrix (#354230) and maintained in Complete mTeSR Medium (Basal medium with supplements) (StemCell Technologies, #05850). Three iPSC clones, from three individual donors, were treated with 250 ng/mL GFP mRNA lipid particles and 100 ng/mL ApoE for a period of 48 hours. Human Neural progenitor cells (NPCs) and Culture NPCs are immature neuronal cell types derived from induced pluripotent stem cells, that can be differentiated to mature cortical neurons using specific culture conditions, reagents and cell culture media which promote differentiation. The differentiation process from iPSC clones to functionally and physiologically-defined mature cortical neurons is a time-consuming and technically-challenging process. Commercially-available NPCs accelerate the process of neuronal culture, as these cell types are further along in the differentiation pathway. In these studies, well-characterized NPCs were purchased from StemCell Technologies (Vancouver, Canada, Female cell line Cat #70902, Male line: StemCell Technologies Cat #70901.) and cultured to derive mature cortical neurons. The lipid particle formulations of the invention can be applied to various points along this differentiation pathway, starting from the progenitor stage to the point of neuronal maturity. This also suggests the possible application of lipid particle-based nucleic acid vectors to genetic manipulation of iPSCs themselves, or neuronal cell types upstream of the NPC stage.

NPCs were maintained by seeding them on Matrigel™ coated cell culture flasks with Neural Progenitor Medium 2 (StemCell Technologies Cat. #08560). Full media changes were performed every other day until the cells were confluent, approximately every 4 days, at which time they were passaged. NPCs were treated 24 hours after seeding on Matrigel™ coated 24 well plates with 1 ug/mL of ApoE and 100 ng/mL of the plasmid lipid particle formulations.

Differentiation of NPCs was accomplished in BrainPhys™ Neuronal Medium N2-A & SM1 Kit cat#05793. Differentiation was performed using a modified version of the StemCell BrainPhys™ protocol, in short: on Day 0 of differentiation, NPCs were seeded on Poly-L-Ornithine and laminin coated T25 tissue culture flasks in Neural Progenitor Medium 2. Twenty-four hours later, the media was switched to neuron differentiation media (STEMdiff™ Neuron Differentiation Kit Cat. #08500, StemCell), and full media changes were performed every other day following.

On Day 6 of differentiation, the cells were passaged into Poly-L-Ornithine and Laminin coated 24 well culture dishes with half of the normal quantity of STEMdiff™ Media. This becomes Day 0 of neuron maturation. Twenty-four hours later, on day 1 of neuron maturation, half of the normal quantity of BrainPhys™ Neuronal Medium was added, and ½ media changes were performed with BrainPhys™ Neuronal Medium every other day for the duration of the experiment.

Treatment of Neurons and assessment using the IncuCyte™ S3 Live Cells Scope

When the neurons matured to the required day (day 1, 7, 10, 14, etc.), 1 ug/mL of ApoE was added to each well followed by 600 ng/mL of the nucleic acid therapeutic in Lipid Mix formulations. The treated plate was then analysed in real time using the IncuCyte™ S3 Live-Cell Analysis System (Essen Biosciences, Ann Arbor, Mich., USA) which was situated inside the cell culture incubator. The IncuCyte™ S3 was programed to take an image at the 10× magnification at 6 fields locations within each well, every 6 hours for the duration of the experiment. Following data acquisition, an algorithm was created using the IncuCyte™ S3 software to identify cell bodies and % confluence for both the phase contrast and Green Fluorescent Protein ("GFP") images.

The following examples are provided for the purpose of illustrating, not limiting, the invention.

Example 1

Microfluidic Mixing of Nucleic Acid Therapeutics (NAT) into Lipid Nanoparticles (LNP)

Lipid Mix solutions were prepared in ethanol by combining prescribed amounts of lipids (see Table 1) from individual lipid stocks in ethanol. For NanoAssemblr™ SPARK methodology, a lipid mix solution concentration of 50 mM was used, and for the NanoAssemblr™ Benchtop, a lipid mix solution of 12.5 mM was typically used.

MessengerRNA (mRNA) or plasmid NAT was diluted using sodium acetate buffer to the required concentration. Lipid particle samples were then prepared by running both fluids using the NanoAssemblr™ Spark instrument. Briefly, 10-20 μg of nucleic acids in 100 mM sodium acetate buffer in a total volume of 36 μL was mixed with 12 μL of 50 mM lipid mix solution as required by the N/P ratios (4 or 6). The microfluidically mixed nanoparticles were immediately diluted down with the 48 μL Ca and Mg free 1× PBS at pH 7.4 in the aqueous output well. These nucleic acid Lipid particle were immediately collected into micro centrifuge tubes containing 96 μL of Ca and Mg free 1× PBS at pH 7.4. Encapsulation efficiency was measured by a modified Ribogreen/Picogreen™ assay. Observed particle attributes were generally in the range of 140-300 nm for plasmid, depending on lipid composition.

Lipid based formulations were also manufactured by NanoAssemblr™ Benchtop for testing. Briefly, 350 μL of mRNA/plasmid was diluted using 100 mM sodium acetate buffer to the required concentration of 0.2 to 0.3 mg/mL depending on N/P ratio of 6 or 4. Lipid particle samples were then prepared by running both fluids, namely, nucleic acids in aqueous solvent and Lipid Mix in ethanol at a flow ratio of 3:1 and at total flow rate of 12 ml/minute. Following mixing in the microfluidic device, the post cartridge Lipid particle sample was diluted into RNAse free tubes containing three to 40 volumes of phosphate buffered saline (PBS) buffer, pH 7.4. Ethanol was finally removed through dialysis in PBS, pH 7 or using Amicon™ centrifugal filters (Millipore, USA) at 3000 RPM, or using TFF systems. Once the required concentration was achieved, the particles were filter sterilized using 200 μm filters in aseptic conditions. Final NAT encapsulation efficiency was measured by Ribogreen assay.

Components of the Lipid Mixes

Ionizable lipid 1,17-bis(2-octylcyclopropyl)heptadecan-9-yl 4-(dimethylamino)butanoate hydrochloride, neutral lipid DOPE, and stabilizing agent Myrj52 (Polyoxyethylene (40) stearate) were components of Lipid Mix A. DODMA was used in place of 1,17-bis(2-octylcyclopropyl)heptadecan-9-yl 4-(dimethylamino)butanoate hydrochloride for Lipid Mix A DODMA, and Coatsome™ was used in the Lipid Mix A-COATSOME. The stabilizing agent Myrj was replaced with first a single surfactant, then two surfactants, then three.

(Lipid Mix T20, namely polyoxyethylene (20) sorbitan monolaurate), Lipid Mix T80 (polyoxyethylene (80) sorbitan monolaurate), and Lipid Mix TDM (just Tridecyl β-D-maltoside or "TBD"). In Lipid Mix K and L, the stabilizing agent was polyoxyethylene (20) sorbitan monolaurate: polyoxyethylene (80) sorbitan monolaurate: Tridecyl β-D-maltoside combination in a 1:1:1 wt/wt ratio. In all formulations, 0-0.1 Mol % of DiD label was present. A list of component ratios for the Lipid Mixes is shown in Table 1.

TABLE 1

Components and Ratios of Lipid Mixes

| Name | Components |
|---|---|
| Lipid mix A | 50/10/37.5/2.5<br>IL*/DSPC/cholesterol/Myrj52 |
| Lipid mix D | 40/40/17.5/17.5/2.5<br>IL/DOPE/cholesterol/Myrj52 |
| Lipid Mix TBD | 40/20/37.4/2.5<br>IL/DOPE/cholesterol/Tridecyl-β-D-maltoside |
| Lipid Mix T20 | 40/20/37.4/2.5<br>IL/DOPE/cholesterol/polyoxyethylene (20) sorbitan monolaurate** |
| Lipid Mix T80 | 40/20/37.4/2.5<br>IL/DOPE/cholesterol/polyoxyethylene (80) sorbitan monolaurate*** |
| LNP Tween20 | 40/20/39/1<br>IL/DOPE/cholesterol/polyoxyethylene (20) sorbitan monolaurate** |

TABLE 1-continued

Components and Ratios of Lipid Mixes

| Name | Components |
|---|---|
| LNP Tween80 | 40/20/39/1 IL/DOPE/cholesterol/polyoxyethylene (80) sorbitan monolaurate*** |
| Lipid Mix K | 40/20/37.4/2.5 IL/DOPE/cholesterol/(polyoxyethylene (20) sorbitan monolaurate/polyoxyethylene (80) sorbitan monolaurate/Tridecyl-β D-maltoside in equal weight ratios). |
| Lipid Mix L | 40/20/35.9/4 IL/DOPE/cholesterol/Lipid H (polyoxyethylene (20) sorbitan monolaurate/polyoxyethylene (80) sorbitan monolaurate/Tridecyl-β D-maltoside in equal weight ratios). |
| Lipid Mix M | 40/20/39/polyoxyethylene (80) sorbitan monolaureate 0.5 Mol %, polyoxyethylene (20) sorbitan monolaurate 0.5 Mol % |

*IL is: ionizable lipid. BOCHD-C3-DMA, DODMA, and Coatsome ™ were IL in various examples. The suffix DODMA or COATSOME after Lipid Mix A or Lipid Mix K is used to signify where these lipids were used. In all other situations, IL is BOCHD-C3-DMA.
**also known as Polysorbate 20 or Tween 20
***is also known as Polysorbate 80 or Tween 80

Example 2

Lipid Particle or "LNP" Characterization and Encapsulation

Particle size (hydrodynamic diameter of the particles) was determined by Dynamic Light Scattering (DLS) using a ZetaSizer Nano ZS™, Malvern Instruments, UK). He/Ne laser of 633 nm wavelength was used as the light source. Data were measured from the scattered intensity data conducted in backscattering detection mode (measurement angle 173). Measurements were an average of 10 runs of two cycles each per sample. Z-Average size was reported as the lipid particle size, and is defined as the harmonic intensity averaged particle diameter.

The results of the plasmid and mRNA encapsulation for various Lipid Mixes described in the application are shown in Table 2. There was good encapsulation in all the formulations, with polydispersity under 0.3.

TABLE 2A

Plasmid LNP Particles produced using the NanoAssemblr ™ SPARK micromixer: Physico-chemical parameters

| Formulations | Size | PDI | Encapsulation Efficiency (%) |
|---|---|---|---|
| LIPID MIX A pDNA LNP N/P 6 | 180 | 0.27 | 92 |
| LIPID MIX D pDNA LNP N/P 6 | 144 | 0.28 | 94 |
| LIPID MIX T20 pDNA LNP N/P 6 | 161 | 0.1 | 99 |
| LIPID MIX T80 pDNA LNP N/P 6 | 144 | 0.12 | 98 |
| LIPID MIX K pDNA LNP N/P 6 | 193 | 0.10 | 99 |
| LIPID MIX L pDNA LNP N/P 6 | 191 | 0.11 | 99 |
| LIPID MIX A pDNA LNP N/P 4 | 124 | 0.21 | 68 |
| LIPID MIX D pDNA LNP N/P 4 | 150 | 0.26 | 94 |
| LIPID MIX T20 pDNA LNP N/P 4 | 178 | 0.24 | 92 |
| LIPID MIX T80 pDNA LNP N/P 4 | 141.3 | 0.02 | 95 |
| LIPID MIX K pDNA LNP N/P 4 | 175 | 0.08 | 99 |
| LIPID MIX L pDNA LNP N/P 4 | 160 | 0. | 98 |
| Lipid Mix TBD pDNA N/P 6 | >500 | N/A | 99 |
| Lipid Mix K mRNA LNP N/P 4 | 151 | 0.10 | 99 |
| Lipid Mix L mRNA LNP N/P 4 | 127 | 0.14 | 94 |

TABLE 2B mRNA LNP and plasmid LNP particles produced using NanoAssemblr ™ Benchtop micromixer: Physico-chemical parameters

| Formulations | Size (nm) | PDI | Encapsulation Efficiency (%) |
|---|---|---|---|
| Lipid Mix K pDNA N/P 6 | 149 | 0.08 | 81 |
| Lipid Mix L pDNA N/P 6 | 126 | 0.06 | 97 |
| Lipid Mix K mRNA N/P 6 | 142 | 0.09 | 96 |
| Lipid Mix L mRNA N/P 6 | 131 | 0.07 | 98 |

Example 3

Treatment of Neurons with Plasmid LNP and Assessment using IncuCyte™ S3—GFP Expression Plasmid preparation pCX-EGFP Plasmid size 5514 nt, SEQ ID NO. 1, custom made by GenScript USA Inc, Piscataway, N.J., including ampicillin resistance, restriction enzyme HINDIII, in ddH$_2$O, was used for this assessment. The plasmid included a GFP expressing component which produces target protein only when the plasmid is expressed within a cell.

Turning now to the cell treatment using lipid particle: when a pure neuronal population was ready, usually around day 8 of neural differentiation, 1 ug/mL of ApoE and 600 ng/mL of the plasmid lipid particle were added with Neural Maintenance-XF™ culture medium (Axol Bioscience). The treated plate was then placed in the IncuCyte™ S3 instrument located within the cell culture incubator. The IncuCyte™ S3 took 10× images at 6 locations within each well every 6 hours for the duration of the experiment. Following data acquisition, an algorithm was created using the IncuCyte™ S3 software to identify neuron cell bodies and neurites for both the phase and GFP images.

To create FIGS. 1A-1F, we used GFP mask, an image analysis tool for marking regions within a cell that are positive for the GFP fluorescent signal, and then we used a negative image for better black and white reproduction. The images were taken at 72 hours post treatment, DIV14. The GFP-positive cell bodies and neuritis are clearly seen.

Figure 1A:
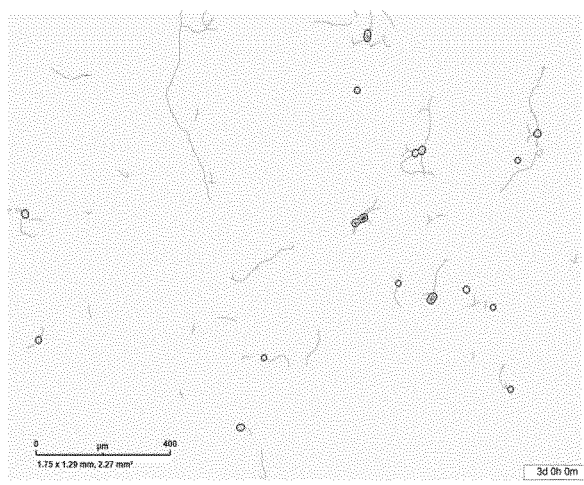
FIG. 1A-1F are black and white negative renditions of "GFP mask" phase contrast images of DIV 14 mature neurons derived from human neural progenitor cells and which have been transfected with plasmid GFP-LNP prepared using LIPID MIX A (FIG. 1A), LIPID MIX TBD (FIG. 1B), LIPID MIX T20 (FIG. 1C), LIPID MIX T80 (FIG. 1D), LIPID MIX K (FIG. 1E), and LIPID MIX L (FIG. 1F). The plasmid-GFP lipid particles (lipid (N)
Figure 1B:
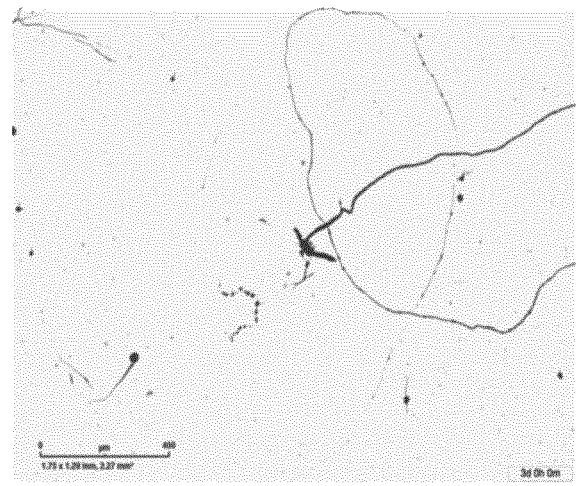
Figure 1C:
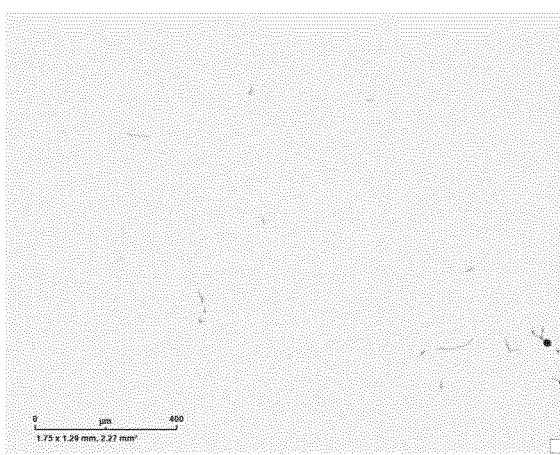
Figure 1D:
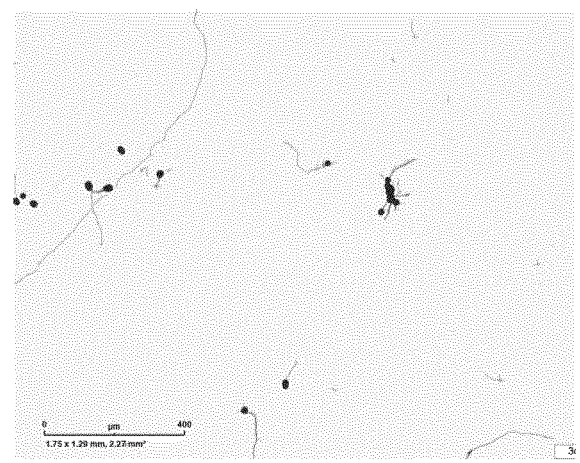
Figure 1E:
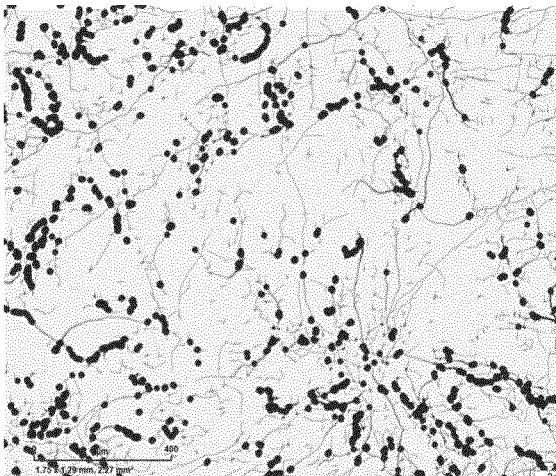
Figure 1F:
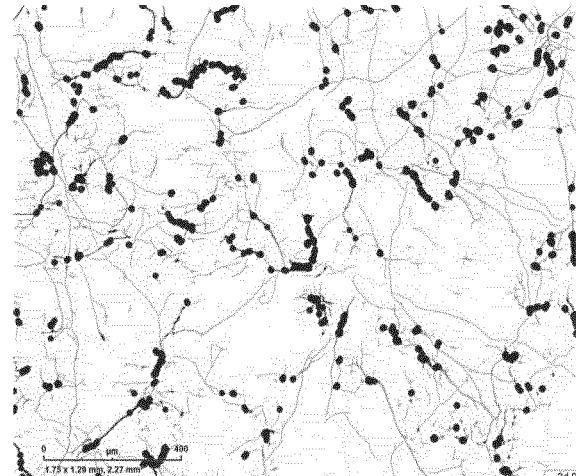

The formulations tested were: FIG. 1A LIPID MIX A, FIG. 1B LIPID MIX D, FIG. 1C LIPID MIX T20, FIG. 1D LIPID MIX T80, FIG. 1E LIPID MIX K, FIG. 1F LIPID MIX L. The amino lipid to nucleotide phosphate mol ratio is N/P 4. It is clear that although the individual surfactants Polysorbate 20, Polysorbate 80, and the maltoside did not make a large positive impact on transfection or cell viability, the combination of all three did.

Example 4

Effects of the Formulations on Cellular Health

As a point of reference, FIG. 2 is a phase contrast image of untreated mature neurons on day 14 (DIV14) of neuron maturation. FIGS. 3A, 3B, and 3C are phase contrast images of iPSC-derived neurons, at DIV 14, untreated and at 48 hours following treatment with Lipid particle consisting of LIPID MIX A or LIPID MIX L containing plasmid encoding GFP at The amino lipid to nucleotide phosphate mol ratio N/P 6. Data shown is from the Incucyte™ live imaging instrument. Observations: White round cells in a phase contrast image show dead/dying cells; images of the Lipid Mix A show that the formulation is toxic to the human iPSC-derived neurons; and Lipid mix L is very similar to untreated cells (i.e., no toxicity).

FIG. 4A-D are phase contrast images of iPSC-derived neural progenitor cells, at DIV 3 untreated, and at 48 hours following treatment with lipid particles consisting of no treatment (FIG. 4A), LIPID MIX A GFP plasmid (FIG. 4B), LIPID MIX L GFP plasmid (FIG. 4C) or Lipofectamine™ plasmid (FIG. 4D), all at DNA:lipid ratio N/P 6, as taken with the Incucyte™ instrument. White round cells in a phase contrast image are dead or dying cells. Images of the Lipid Mix A test show that the formulation is toxic to the human iPSC-derived neural progenitor cells (NPC). Lipid Mix L appears less toxic to cells; and Lipofectamine™ is toxic. Toxicity is indicated by the number of viable cells, with fewer cells meaning higher toxicity.

Example 5 iPSC-Derived Mature Neurons Confirmed as Such with Flow Cytometry

Following treatment and incubation of neurons, the media from each well was collected and the cells were harvested using 0.25% trypsin inactivated with 3% FBS in PBS, and pelleted in their corresponding media. Following centrifugation, the cells were washed once with PBS and again pelleted. The cells were then resuspended in Binding Buffer™ (BD Biosciences), and Propidium Iodide was added to stain for cells with completely ruptured membranes (dead cells). The cells were then assessed using a BD Biosciences Canto™ II flow cytometer.

The marker panel consisted of βIII tubulin (TUJ1), which is a neuronal lineage marker present in differentiated (mature) neurons, doublecortin (DCX), which is expressed in early stages of neuronal differentiation, and Sox 1, which is expressed in neural progenitor cells (undifferentiated neurons).

TABLE 3

| Flow Cytometry Characterization of Neurons at DIV14 | | |
| --- | --- | --- |
| Marker | Marker specificity | % of culture |
| βIII tubulin & doublecortin | Neurons (mature) | 74 |
| Doublecortin & SOX1 negative | Neurons (early) | 54.3 |

Flow cytometry data showed that the majority of the differentiated neuron populations (74%) expressed markers specific to mature neurons prior to treatment, confirming that the tested neurons were substantially mature.

Example 6

Treatment of Neurons and Assessment of Neuron Viability

Cell viability and neurite outgrowth are the most commonly measured indications of neural cell health and function. Neural cells subjected to cytotoxic treatments often respond by shortening their neurites. Also, neurite outgrowth is gold-standard marker for a neuronal culture that is viable. The unit of measurement for neurite length is $mm/mm^2$. "Average neurite length" is derived from data from all the images of a well, looking at the length of neurites per $mm^2$.

"Cell body cluster" is a measure of the number of cell bodies. Treated cells should have similar cell body numbers as untreated to show lack of toxic effects. The unit of measurement is $1/mm^2$. The average number of cell bodies across all the images of a well is calculated by looking at the number of identified cell bodies per $mm^2$.

A measurement used to show transfection by the different Lipid Mixes, and expression by the NAT, is "% GFP positive cell body clusters". This measurement normalizes the GFP cell cluster values to the number of total cell bodies in an image and gives an overall estimate of the number of GFP positive neurons in the image.

Mature neuron cells were treated on DIV 14 of maturity. LIPID MIX A, LIPID MIX TBD, LIPID MIX T20, LIPID MIX T80, LIPID MIX K, and LIPID MIX L were mixed with GFP plasmid at a 4× weight ratio of nucleic acid to lipid.

The number of GFP-positive cell bodies and the total length of GFP-positive neurites was measured. Data from these two graphs are shown in FIG. 5 and FIG. 6. LIPID MIX K & LIPID MIX L formulations show the highest number of GFP-positive cell bodies and neurites, resulting in the highest % GFP-positive in mature iPSC-derived neurons, relative to LIPID MIX A/untreated. The results from the cell body count and phase neurite length (FIG. 5) confirmed those of the GFP % results (FIG. 6).

Example 7 mRNA Transfection

Induced pluripotent stem cells (iPSCs) were generated from reprogrammed donor-derived fibroblasts using non-integrating oriP/EBNA1{Yu, 2009, Human induced pluripotent stem cells free of vector and transgene sequences} plasmids. Cells were maintained on Corning® Growth Factor Reduced (GFR) Basement Membrane Matrix (#354230) and maintained in Complete mTeSR Medium (Basal medium with supplements) (StemCell Technologies, #05850). Three iPSC clones, from three individual donors, were treated with 250 ng/mL GFP mRNA (CleanCap® EGFP mRNA CleanCap® Enhanced Green Fluorescent Protein mRNA (Trilink Biotechnologies, San Diego, Calif.)) lipid particles and 100 ng/mL ApoE for a period of 48 hours. The 996 bp mRNA is represented as Seq Id No. 2. The total number of cells were determined using a DAPI nuclear label, and the percentages of GFP-expressing cells relative to the total number of cells per well were then calculated. As shown in FIG. 7, the lipid particles made from Lipid Mix L showed the highest ratio of GFP-expressing iPSCs as compared to the untreated and Lipid Mix A groups (40.4% vs 8.36%). The graph represents the mean percentage GFP-positive cells per treatment group. This experiment illustrates that mRNA as well as plasmid transfection is favorably accomplished by the lipid mixes of the invention, and that iPSC can be successfully transfected.

Example 8

Plasmid Transfection In Vitro, GFP Expression

Plasmid and lipid particle preparation was as specified above. In this experiment, different ratios of the ionizable lipid, neutral lipid, cholesterol and surfactant(s) were used with plasmid encapsulation. Please see Table 1 for details on the described formulations. LNP Tween 20 and LNP Tween 80 had a slightly different ratio of cholesterol and stabilizing agent than that used for mRNA Lipid Mix T20 and T80. The purpose of the experiment was to study the effect of plasmid mediated expression of GFP in neural progenitor cells (NPC) in vitro using lipid particle compositions with individual surfactant versus the combination, and in a second part, different surfactants as single agents versus a standard surfactant Myrj52. Transfection activity mediated by formulations comprising 1 mol % Tween 20, 1 mol % tween 80, and 1 mol % of a one to one combination of tween 20 and tween 80 in lipid particles are shown in FIG. 8A. The combination of the two Tweens worked better than each one individually to instill GFP protein expression in the cells.

For the second part of the experiment, transfection activity mediated by formulations comprising 2.5 mol % Myrj52 (Lipid Mix A), 2.5 mol % polysorbate 20 (Tween 20 in Lipid Mix T20) and 2.5 mol % polysorbate 80 (Tween 80 in Lipid Mix T80), in lipid particles are shown in FIG. 8B. Both polysorbate 20 and polysorbate 80 worked better than Myrj52 to instill GFP protein expression in the cells.

Example 9

Effects of Surfactant Combination Present Regardless of Ionizable Lipid Identity NPC were exposed to alternate ionizable lipid containing forms of Lipid Mix A and Lipid Mix K encapsulated mRNA to identify any ionizable lipid specific effect. FIG. 9A shows mRNA expression as a percent of GFP for Lipid Mix A and Lipid Mix A DODMA compared to Lipid Mix K and Lipid Mix K DODMA. Similar results are seen for Lipid Mixes made with 1,17-bis(2-octylcyclopropyl)heptadecan-9-yl 4-(dimethylamino)butanoate HCl as opposed to DODMA.

FIG. 9B shows mRNA mediated expression of GFP (Mean Fluorescence Intensity) in neural progenitor cells using similar pattern of testing, but with COATSOME™ as the ionizable lipid. Again, Lipid Mix K with 1,17-bis(2-octylcyclopropyl)heptadecan-9-yl 4-(dimethylamino)butanoate HCl or Coatsome™ was better than Lipid Mix A or Lipid Mix A Coatsome™.

The benefit of the combined surfactants in Lipid Mix K was maintained whether the ionizable lipid was 1,17-bis(2-octylcyclopropyl)heptadecan-9-yl 4-(dimethylamino)butanoate HCl, DODMA or Coatsome™.

Example 10

Transfectamine™ transfecting agent (Life Technologies Inc.) was compared to Lipid Mix K and Lipid Mix L (1,17-bis(2-octylcyclopropyl)heptadecan-9-yl 4-(dimethylamino)butanoate HCl) in NPCs for its effect on cell health. The results are shown in FIG. 10. After 144 hours of normal cell culture including passages, cells treated with Lipofectamine™ were nonviable, whereas those treated with Lipid Mix K and L were almost 100% confluent.

Example 11

Two commonly used ionizable lipids, KC2 and DLin-MC3-DMA, were substituted for the ionizable lipid component for Lipid Mixes A and K. NPC were transfected as specified above, and the results at 48 H for GFP Median Fluorescent Intensity via flow cytometry are shown in FIG. 11. For reference, the alipid particle size, PDI, and encapsulation efficiency are listed in Table 4. Both KC2 and DLin-MC3-DMA (MC3 in the graph) were effective in the Lipid Mix K to enhance GFP expression over the control Lipid Mix A. PNI-IL-1 is 1,17-bis(2-octylcyclopropyl)heptadecan-9-yl 4-(dimethylamino)butanoate HCl).

| Ionizable Lipid | Lipid Particle Size | PDI | Encapsulation Efficiency % |
|---|---|---|---|
| PNI-IL-1-A | 131.95 | 0.225 | 76.7 |
| PNI-IL-1-K | 219.1 | 0.0685 | 99 |
| MC3-A | 113.45 | 0.166 | 97.6 |
| MC3-K | 233.7 | 0.1345 | 99 |
| KC2-A | 115.8 | 0.1175 | 91.9 |
| KC2-K | 229.1 | 0.0115 | 99.7 |

While specific embodiments of the invention have been described and illustrated, such embodiments should be considered illustrative of the invention only and not as limiting the invention as construed in accordance with the accompanying claims.

BIBLIOGRAPHY

Akhtar, S., E. Basu S Fau-Wickstrom, R. L. Wickstrom E Fau-Juliano and R. L. Juliano (1991). "Interactions of antisense DNA oligonucleotide analogs with phospholipid membranes (liposomes)." (0305-1048 (Print)).

Kauffman, K. J., M. J. Webber and D. G. Anderson (2015). "Materials for non-viral intracellular delivery of messenger RNA therapeutics." J Control Release.

Kaufmann k, Dorkin Robert J; Yang, Jung H; Heartlein, Michael W; De Rosa, Frank; Mir, Faryal F; Fenton, Owen S; Anderson, Daniel G (2015). "Optimization of Lipid Nanoparticle Formulations for mRNA Delivery in Vivo with Fractional Factorial and Definitive Screening Designs." Nano Letters 15: 7300-7306.

Lv, H., S. Zhang, B. Wang, S. Cui and J. Yan (2006). "Toxicity of cationic lipids and cationic polymers in gene delivery." Journal of Controlled Release 114(1): 100-109.

Mingozzi, F. and K. A. High (2013). "Immune responses to AAV vectors: overcoming barriers to successful gene therapy." Blood 122(1): 23-36.

O'Mahony, A. M., B. M. Godinho, J. F. Cryan and C. M. O'Driscoll (2013). "Non-viral nanosystems for gene and small interfering RNA delivery to the central nervous system: formulating the solution." J Pharm Sci 102(10): 3469-3484.

Tam, Y. Y., S. Chen and P. R. Cullis (2013). "Advances in Lipid Nanoparticles for siRNA Delivery." Pharmaceutics 5(3): 498-507.

What is claimed is:

1. A transfection reagent composition comprising:
    35-50 Mol % of a cationic ionizable lipid, or a pharmaceutically acceptable salt thereof;
    15 to 25 Mol % structural lipid;
    35 to 41 Mol % sterol; and
    0.5 to about 10 Mol % of a stabilizing agent, wherein the stabilizing agent is a maltoside and comprises more than one surfactant.

2. The composition of claim 1, wherein the cationic ionizable lipid is an amino lipid or a pharmaceutically acceptable salt thereof.

3. The composition of claim 1, wherein the stabilizing agent includes a polysorbate.

4. The composition of claim 3, wherein the polysorbate is polysorbate (80).

5. The composition of claim 1, wherein the stabilizing agent includes a mixture of polysorbates.

6. A transfection reagent composition comprising:
    35-50 Mol % of a cationic ionizable lipid, or a pharmaceutically acceptable salt thereof;
    15 to 25 Mol % structural lipid:
    35 to 41 Mol % sterol; and
    0.5 to about 10 Mol % of a stabilizing agent comprising a mixture of polysorbate and maltoside.

7. The composition of claim 6, wherein the stabilizing agent is a mixture of polysorbate 80, polysorbate 20, and Tridecyl-D-maltoside.

8. The composition of claim 7 wherein the mixture is an equal ratio of polysorbate 80, polysorbate 20, and Tridecyl-D-maltoside.

9. The composition of claim 1, wherein the cationic ionizable lipid comprises about 40 Mol % of the composition.

10. The composition of claim 1, wherein the stabilizing agent comprises about 0.5 to 5 Mol % of the composition.

11. The composition of claim 1, wherein the sterol is cholesterol.

12. The composition of claim 1, further comprising a nucleic acid or a peptide.

13. The composition of claim 12, wherein the nucleic acid is a DNA, an RNA, or a plasmid capable of expressing an RNA.

14. The composition of claim 1, wherein cationic the ionizable lipid is selected from the group consisting of BOCHD-C3-DMA, KC2, MC3, a-D-Tocopherolsuccinoyl and DODMA, or a pharmaceutically acceptable salt thereof.

15. The composition of claim 1, wherein the structural lipid is selected from the group consisting of 1,2-dioleoyl-sn-glycero-3-phosphoethanolamine (DOPE), DSPE, or DSPC.

16. The composition of claim 1, wherein the composition exists in the form of lipid nanoparticles having a diameter of from about 15 nm to about 300 nm.

17. A method for transfecting a cell with a nucleic acid therapeutic while maintaining activity of the nucleic acid and viability of the cell, comprising contacting the cell with the composition of claim 1.

18. The method of claim 17, wherein the cell is a mammalian cell.

19. The method of claim 17, wherein the cell is a human-derived cell type.

* * * * *